(12) United States Patent
Girouard et al.

(10) Patent No.: US 7,627,373 B2
(45) Date of Patent: Dec. 1, 2009

(54) METHOD AND APPARATUS FOR CELL AND ELECTRICAL THERAPY OF LIVING TISSUE

(75) Inventors: Steven D. Girouard, Woodbury, MN (US); Rodney W. Salo, Fridley, MN (US); Bruce H. KenKnight, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 384 days.

(21) Appl. No.: 10/723,258

(22) Filed: Nov. 25, 2003

(65) Prior Publication Data

US 2004/0158290 A1 Aug. 12, 2004

Related U.S. Application Data

(60) Provisional application No. 60/429,954, filed on Nov. 30, 2002.

(51) Int. Cl.
*A61N 1/00* (2006.01)
(52) U.S. Cl. .......................................................... 607/9
(58) Field of Classification Search ................ 607/9–28
See application file for complete search history.

(56) References Cited

U.S. PATENT DOCUMENTS

| | | | |
|---|---|---|---|
| 3,692,027 A | 9/1972 | Ellinwood, Jr. | 128/260 |
| 4,003,379 A | 1/1977 | Ellinwood, Jr. | 128/260 |
| 4,146,029 A | 3/1979 | Ellinwood, Jr. | 128/260 |
| 4,202,340 A | 5/1980 | Langer et al. | 128/419 |
| 4,271,192 A | 6/1981 | Wurtman et al. | 424/319 |
| 4,281,664 A | 8/1981 | Duggan | 128/696 |
| 4,299,220 A | 11/1981 | Dorman | 128/260 |
| 4,470,987 A | 9/1984 | Wurtman et al. | 424/259 |
| 4,544,371 A | 10/1985 | Dormandy, Jr. et al. | 604/891 |
| 4,556,063 A | 12/1985 | Thompson et al. | 128/419 PT |
| 4,559,946 A | 12/1985 | Mower | 128/419 D |

(Continued)

FOREIGN PATENT DOCUMENTS

EP 0054138 10/1981

(Continued)

OTHER PUBLICATIONS

Buchwald, A B., et al., "Decoy Oligodeoxynucleotide Against Activator Protein-1 Reduces Neointimal Proliferation After Coronary Angioplasty in Hypercholesterolemic Minipigs", *Journal of the American College of Cardiology*, 39 (4), (Feb. 20, 2002),732-738.

(Continued)

*Primary Examiner*—Scott M Getzow
(74) *Attorney, Agent, or Firm*—Schwegman, Lundberg & Woessner, P.A.

(57) ABSTRACT

A method for cell and electrical therapy of living tissue including administration of exogenous cells into a region of injured tissue and application of electrical energy. In one application the combined cell and electrical therapy is applied in vivo to damaged heart tissue. In such applications, minimally invasive procedures are used to apply the cell therapy and the electrical therapy is provided via an implantable pulse generator. In one application an implantable pacemaker is used in the VDD mode with an atrioventricular delay kept relatively short when compared to the intrinsic atrioventricular delay.

23 Claims, 10 Drawing Sheets

U.S. PATENT DOCUMENTS

| | | |
|---|---|---|
| 4,651,716 A | 3/1987 | Forester et al. ............... 128/1 D |
| 4,674,518 A | 6/1987 | Salo ............................ 128/695 |
| 4,677,989 A | 7/1987 | Robblee |
| 4,686,987 A | 8/1987 | Salo et al. ............. 128/419 PG |
| 4,693,253 A | 9/1987 | Adams .................... 128/419 D |
| 4,787,389 A | 11/1988 | Tarjan ................... 128/419 PG |
| 4,790,317 A | 12/1988 | Davies ....................... 128/419 |
| 4,871,351 A | 10/1989 | Feingold ...................... 604/66 |
| 4,880,005 A | 11/1989 | Pless et al. ............ 128/419 PG |
| 4,897,987 A | 2/1990 | Spalla ........................ 56/16.7 |
| 4,902,508 A | 2/1990 | Badylak et al. |
| 4,904,472 A | 2/1990 | Belardinelli et al. ........ 514/263 |
| 4,924,875 A | 5/1990 | Chamoun ................... 600/509 |
| 4,930,075 A | 5/1990 | Kortas ................... 364/413.06 |
| 4,938,231 A | 7/1990 | Milijasevic et al. |
| 4,940,054 A | 7/1990 | Grevis et al. .......... 128/419 PG |
| 4,944,299 A | 7/1990 | Silvian ................. 128/419 PG |
| 4,949,719 A | 8/1990 | Pless et al. .................. 128/419 |
| 4,980,379 A | 12/1990 | Belardinelli et al. ........ 514/821 |
| 4,987,897 A | 1/1991 | Funke ................. 128/419 PG |
| 5,002,052 A | 3/1991 | Haluska .......................... 607/4 |
| 5,014,698 A | 5/1991 | Cohen ....................... 128/419 |
| 5,031,621 A | 7/1991 | Grandjean et al. |
| 5,040,533 A | 8/1991 | Fearnot ................ 128/419 PG |
| 5,041,107 A | 8/1991 | Heil, Jr. ................... 604/891.1 |
| 5,042,497 A | 8/1991 | Shapland .................... 600/509 |
| 5,058,581 A | 10/1991 | Silvian ................. 128/419 PG |
| 5,087,243 A | 2/1992 | Avitall .......................... 604/20 |
| 5,109,842 A | 5/1992 | Adinolfi |
| 5,113,869 A | 5/1992 | Nappholz et al. ............ 128/696 |
| 5,127,404 A | 7/1992 | Wyborny et al. ......... 128/419 P |
| 5,130,141 A | 7/1992 | Law et al. |
| 5,135,004 A | 8/1992 | Adams et al. ............... 128/696 |
| 5,137,019 A | 8/1992 | Pederson et al. ............ 128/419 |
| 5,179,945 A | 1/1993 | Hofwegen et al. .......... 128/419 |
| 5,179,946 A | 1/1993 | Weiss ..................... 128/419 D |
| 5,184,614 A | 2/1993 | Collins et al. ......... 128/419 PG |
| 5,188,105 A | 2/1993 | Keimel ....................... 128/419 |
| 5,190,035 A | 3/1993 | Salo et al. ................... 128/419 |
| 5,193,535 A | 3/1993 | Bardy et al. ............ 128/419 D |
| 5,199,428 A | 4/1993 | Obel et al. ............... 128/419 C |
| 5,215,083 A | 6/1993 | Drane et al. ................ 128/419 |
| 5,220,917 A | 6/1993 | Cammilli et al. ........ 128/419 D |
| 5,251,621 A | 10/1993 | Collins ........................... 607/4 |
| 5,259,380 A | 11/1993 | Mendes et al. |
| 5,269,301 A | 12/1993 | Cohen ............................ 607/6 |
| 5,275,826 A | 1/1994 | Badylak et al. |
| 5,282,836 A | 2/1994 | Kreyenhagen et al. ......... 607/4 |
| 5,284,136 A | 2/1994 | Hauck et al. ................... 607/24 |
| 5,292,338 A | 3/1994 | Bardy ............................ 607/5 |
| 5,301,677 A | 4/1994 | Hsung ........................ 128/705 |
| 5,305,745 A | 4/1994 | Zacouto ...................... 600/324 |
| 5,312,453 A | 5/1994 | Shelton et al. |
| 5,314,430 A | 5/1994 | Bardy |
| 5,325,856 A | 7/1994 | Nitzsche et al. ............. 128/703 |
| 5,334,222 A | 8/1994 | Salo et al. ..................... 607/17 |
| 5,336,252 A | 8/1994 | Cohen |
| 5,342,408 A | 8/1994 | deCoriolis et al. ............. 607/32 |
| 5,346,506 A | 9/1994 | Mower et al. ................... 607/7 |
| 5,350,406 A | 9/1994 | Nitzsche et al. ............... 607/14 |
| 5,352,463 A | 10/1994 | Badylak et al. |
| 5,353,800 A | 10/1994 | Pohndorf et al. ............. 128/673 |
| 5,354,317 A | 10/1994 | Alt ................................ 607/19 |
| 5,366,485 A | 11/1994 | Kroll et al. ...................... 607/5 |
| 5,368,028 A | 11/1994 | Palti ............................ 128/635 |
| 5,379,776 A | 1/1995 | Murphy et al. ............... 128/705 |
| 5,391,190 A | 2/1995 | Pederson et al. .............. 607/23 |
| 5,404,877 A | 4/1995 | Nolan et al. ................. 128/671 |
| 5,405,362 A | 4/1995 | Kramer et al. ................... 607/5 |
| 5,416,695 A | 5/1995 | Stutman et al. ......... 364/413.02 |
| 5,417,717 A | 5/1995 | Salo et al. ..................... 607/18 |
| 5,423,883 A | 6/1995 | Helland |
| 5,431,682 A | 7/1995 | Hedberg ........................ 607/5 |
| 5,435,999 A | 7/1995 | Austin ....................... 424/93.1 |
| 5,439,483 A | 8/1995 | Duong-Van ..................... 607/5 |
| 5,441,525 A | 8/1995 | Shelton et al. ................ 607/23 |
| 5,456,692 A | 10/1995 | Smith, Jr. et al. ............. 607/31 |
| 5,458,619 A | 10/1995 | Olson ............................. 607/4 |
| 5,460,605 A | 10/1995 | Tuttle et al. ................... 604/67 |
| 5,464,434 A | 11/1995 | Alt ................................. 607/6 |
| 5,476,503 A | 12/1995 | Yang ........................... 607/129 |
| 5,487,752 A | 1/1996 | Salo et al. ..................... 607/17 |
| 5,489,293 A | 2/1996 | Pless et al. ..................... 607/5 |
| 5,496,360 A | 3/1996 | Hoffmann et al. ........... 607/120 |
| 5,499,971 A | 3/1996 | Shapland et al. ............... 604/53 |
| 5,500,008 A | 3/1996 | Fain ............................... 607/5 |
| 5,501,701 A | 3/1996 | Markowitz et al. ............. 607/9 |
| 5,522,853 A | 6/1996 | Kroll ............................. 607/5 |
| 5,531,768 A | 7/1996 | Alferness ....................... 607/6 |
| 5,538,722 A | 7/1996 | Blau et al. ................ 424/93.21 |
| 5,540,723 A | 7/1996 | Ideker et al. .................... 607/7 |
| 5,540,728 A | 7/1996 | Shelton et al. ................ 607/23 |
| 5,545,186 A | 8/1996 | Olson et al. ................... 607/14 |
| 5,545,205 A | 8/1996 | Schulte et al. ............... 607/123 |
| 5,551,953 A | 9/1996 | Lattin et al. ................... 604/20 |
| 5,554,389 A | 9/1996 | Badylak et al. |
| 5,556,421 A | 9/1996 | Prutchi et al. ................. 607/36 |
| 5,562,711 A | 10/1996 | Yerich et al. ................... 607/17 |
| 5,562,713 A | 10/1996 | Silvian ......................... 607/32 |
| 5,571,151 A | 11/1996 | Gregory |
| 5,579,876 A | 12/1996 | Adrian et al. .......... 188/322.17 |
| 5,584,868 A | 12/1996 | Salo et al. ..................... 607/17 |
| 5,586,556 A | 12/1996 | Spivey et al. ................ 600/510 |
| 5,591,215 A | 1/1997 | Greenhut et al. .............. 607/14 |
| 5,602,301 A | 2/1997 | Field |
| 5,603,331 A | 2/1997 | Heemels et al. ............. 128/696 |
| 5,607,418 A | 3/1997 | Arzbaecher ............... 604/891.1 |
| 5,607,463 A | 3/1997 | Schwartz et al. ........... 623/1.44 |
| 5,609,629 A | 3/1997 | Fearnot et al. |
| 5,632,766 A | 5/1997 | Hsu et al. ....................... 607/5 |
| 5,634,899 A | 6/1997 | Shapland et al. ............. 604/51 |
| 5,662,689 A | 9/1997 | Elsberry et al. ................. 607/5 |
| 5,676,686 A | 10/1997 | Jensen et al. ................... 607/9 |
| 5,681,735 A | 10/1997 | Emerson et al. ............. 435/325 |
| 5,683,424 A | 11/1997 | Brown et al. ................... 607/5 |
| 5,690,682 A | 11/1997 | Buscemi et al. ................ 607/3 |
| 5,693,075 A | 12/1997 | Plicchi et al. ................. 607/17 |
| 5,703,125 A | 12/1997 | Bovy et al. .................. 128/637 |
| 5,706,829 A | 1/1998 | Kadri .......................... 128/898 |
| 5,709,215 A | 1/1998 | Perttu et al. ................. 128/708 |
| 5,720,770 A | 2/1998 | Nappholz et al. .............. 607/30 |
| 5,725,561 A | 3/1998 | Stroebel et al. ................. 607/9 |
| 5,725,562 A | 3/1998 | Sheldon ........................ 607/19 |
| 5,730,125 A | 3/1998 | Prutchi et al. ............... 128/637 |
| 5,730,141 A | 3/1998 | Fain et al. ................... 128/705 |
| 5,733,727 A | 3/1998 | Field .............................. 435/6 |
| RE35,779 E | 4/1998 | Alferness et al. ............... 607/5 |
| 5,741,319 A | 4/1998 | Woloszko et al. |
| 5,749,900 A | 5/1998 | Schroeppel et al. ............ 607/4 |
| 5,772,604 A | 6/1998 | Langberg et al. ........... 600/518 |
| 5,782,876 A | 7/1998 | Flammang ..................... 607/4 |
| 5,782,879 A | 7/1998 | Rosborough et al. ........... 607/6 |
| 5,797,967 A | 8/1998 | KenKnight .................... 607/4 |
| 5,800,464 A | 9/1998 | Kieval ............................ 607/9 |
| 5,800,498 A | 9/1998 | Obino et al. ................. 607/123 |
| 5,814,081 A | 9/1998 | Ayers et al. .................... 607/5 |
| 5,817,131 A | 10/1998 | Elsberry et al. ................. 607/5 |
| 5,824,049 A | 10/1998 | Ragheb et al. |
| 5,833,603 A | 11/1998 | Kovacs et al. ............... 600/317 |
| 5,833,978 A | 11/1998 | Tremblay ................. 424/93.7 |
| 5,834,029 A | 11/1998 | Bellamkonda et al. |
| 5,836,935 A | 11/1998 | Ashton et al. ............. 604/891.1 |
| 5,849,033 A | 12/1998 | Mehmanesh et al. |
| 5,855,610 A | 1/1999 | Vacanti et al. |

| Patent | Date | Inventor |
|---|---|---|
| 5,873,904 A | 2/1999 | Ragheb et al. |
| 5,874,420 A | 2/1999 | Pelleg ........................ 514/81 |
| 5,876,353 A | 3/1999 | Riff ............................ 600/547 |
| 5,879,295 A | 3/1999 | Li et al. ..................... 600/373 |
| 5,885,797 A | 3/1999 | Chen et al. ................. 435/69.1 |
| 5,893,881 A | 4/1999 | Elsberry et al. ................ 607/5 |
| 5,899,928 A | 5/1999 | Sholder et al. ................ 607/27 |
| 5,902,324 A | 5/1999 | Thompson et al. |
| 5,913,879 A | 6/1999 | Ferek-Petric et al. .......... 607/14 |
| 5,914,242 A | 6/1999 | Honkanen et al. .......... 435/7.71 |
| 5,916,239 A | 6/1999 | Geddes et al. ................ 607/14 |
| 5,919,210 A | 7/1999 | Lurie et al. .................... 607/3 |
| 5,925,066 A | 7/1999 | Kroll et al. .................... 607/3 |
| 5,928,943 A | 7/1999 | Franz et al. .................. 435/363 |
| 5,945,577 A | 8/1999 | Stice et al. .................... 800/24 |
| 5,949,659 A | 9/1999 | Lesche ........................ 363/16 |
| 5,957,861 A | 9/1999 | Combs et al. ................ 600/547 |
| 5,957,957 A | 9/1999 | Sheldon ........................ 607/17 |
| 5,967,986 A | 10/1999 | Cimochowski et al. ...... 600/454 |
| 5,968,079 A | 10/1999 | Warman et al. ................. 607/5 |
| 5,978,705 A | 11/1999 | KenKnight et al. ............. 607/5 |
| 5,991,660 A | 11/1999 | Goyal ........................ 607/14 |
| 5,991,668 A | 11/1999 | Leinders et al. ............. 607/125 |
| 6,016,447 A | 1/2000 | Juran et al. ................... 607/27 |
| 6,016,448 A | 1/2000 | Busacker et al. ............... 607/29 |
| 6,021,350 A | 2/2000 | Mathson ....................... 607/17 |
| 6,022,322 A | 2/2000 | Prutchi ......................... 600/506 |
| 6,035,233 A | 3/2000 | Schroeppel et al. .......... 600/515 |
| 6,044,297 A | 3/2000 | Sheldon et al. ................ 607/17 |
| 6,048,722 A | 4/2000 | Farb et al. |
| 6,049,735 A | 4/2000 | Hartley et al. ................... 607/9 |
| 6,050,980 A | 4/2000 | Wilson |
| 6,059,726 A | 5/2000 | Lee et al. |
| 6,066,094 A | 5/2000 | Ben-Haim |
| 6,076,015 A | 6/2000 | Hartley et al. .................. 607/20 |
| 6,078,834 A | 6/2000 | Lurie et al. ..................... 607/3 |
| 6,096,070 A | 8/2000 | Ragheb et al. |
| 6,096,347 A | 8/2000 | Geddes et al. |
| 6,099,832 A | 8/2000 | Mickle et al. ............. 424/93.21 |
| 6,100,242 A | 8/2000 | Hammond et al. ............ 514/44 |
| 6,104,949 A | 8/2000 | Pitts Crick et al. .......... 600/547 |
| 6,110,459 A | 8/2000 | Mickle et al. |
| 6,112,116 A | 8/2000 | Fischell et al. |
| 6,112,117 A | 8/2000 | KenKnight et al. ............. 607/5 |
| 6,114,164 A | 9/2000 | Dennis et al. |
| 6,115,636 A | 9/2000 | Ryan ........................ 607/60 |
| 6,128,526 A | 10/2000 | Stadler et al. ............... 600/517 |
| 6,135,976 A | 10/2000 | Tachibana et al. ............. 604/21 |
| 6,140,740 A | 10/2000 | Porat et al. ................... 310/322 |
| 6,151,525 A | 11/2000 | Soykan et al. |
| 6,152,955 A | 11/2000 | KenKnight et al. |
| 6,154,672 A | 11/2000 | Pendekanti et al. ............. 607/5 |
| 6,154,675 A | 11/2000 | Juran et al. ................... 607/29 |
| 6,155,267 A | 12/2000 | Nelson ....................... 128/899 |
| 6,156,572 A | 12/2000 | Bellamkonda et al. |
| 6,161,042 A | 12/2000 | Hartley et al. ................. 607/20 |
| 6,165,164 A | 12/2000 | Hill et al. |
| 6,168,801 B1 | 1/2001 | Heil, Jr. et al. ............... 424/426 |
| 6,174,871 B1 | 1/2001 | Hammond et al. ............ 514/44 |
| 6,198,394 B1 | 3/2001 | Jacobsen et al. ......... 340/573.1 |
| 6,200,265 B1 | 3/2001 | Walsh et al. ................. 600/300 |
| 6,203,495 B1 | 3/2001 | Bardy ........................ 600/301 |
| 6,206,914 B1 | 3/2001 | Soykan et al. ............... 623/1.42 |
| 6,207,451 B1 | 3/2001 | Dennis et al. ................ 435/325 |
| 6,213,942 B1 | 4/2001 | Flach et al. ................. 600/300 |
| 6,221,011 B1 | 4/2001 | Bardy ........................ 600/300 |
| 6,224,566 B1 | 5/2001 | Loeb ............................ 604/22 |
| 6,231,516 B1 | 5/2001 | Keilman et al. ............. 600/485 |
| 6,235,970 B1 | 5/2001 | Stice et al. .................... 800/24 |
| 6,237,398 B1 | 5/2001 | Porat et al. ................. 73/54.09 |
| 6,251,125 B1 | 6/2001 | KenKnight et al. ............. 607/5 |
| 6,254,573 B1 | 7/2001 | Haim et al. ................... 604/157 |
| 6,256,233 B1 | 7/2001 | Glass ..................... 365/189.05 |
| 6,261,230 B1 | 7/2001 | Bardy ........................ 600/300 |
| 6,266,554 B1 | 7/2001 | Hsu et al. .................... 600/515 |
| 6,270,457 B1 | 8/2001 | Bardy ........................ 600/300 |
| 6,272,377 B1 | 8/2001 | Sweeney et al. |
| 6,273,377 B1 | 8/2001 | Archer ........................ 600/515 |
| 6,277,072 B1 | 8/2001 | Bardy ........................ 600/300 |
| 6,277,078 B1 | 8/2001 | Porat et al. .................. 600/486 |
| 6,278,894 B1 | 8/2001 | Salo et al. ................... 600/547 |
| 6,280,380 B1 | 8/2001 | Bardy ........................ 600/300 |
| 6,284,242 B1 | 9/2001 | Kurachi ................... 424/93.21 |
| 6,287,285 B1 | 9/2001 | Michal et al. |
| 6,298,267 B1 | 10/2001 | Rosborough et al. ........... 607/6 |
| 6,298,272 B1 | 10/2001 | Peterfeso et al. ............. 607/120 |
| 6,306,830 B1 | 10/2001 | Hammond et al. ............ 514/44 |
| 6,309,370 B1 | 10/2001 | Haim et al. ................... 604/66 |
| 6,312,378 B1 | 11/2001 | Bardy ........................ 600/300 |
| 6,316,419 B1 | 11/2001 | Leiden et al. ................ 514/44 |
| 6,317,631 B1 | 11/2001 | Ben-Haim et al. ............. 607/9 |
| 6,330,481 B1 | 12/2001 | Van Wijk et al. |
| 6,331,160 B1 | 12/2001 | Bardy ........................ 600/300 |
| 6,336,903 B1 | 1/2002 | Bardy ........................ 600/508 |
| 6,358,202 B1 | 3/2002 | Arent ........................ 600/300 |
| 6,358,203 B2 | 3/2002 | Bardy ........................ 600/300 |
| 6,361,522 B1 | 3/2002 | Scheiner et al. ............... 604/67 |
| 6,361,780 B1 | 3/2002 | Ley et al. ................... 424/400 |
| 6,368,284 B1 | 4/2002 | Bardy ........................ 600/508 |
| 6,370,424 B1 | 4/2002 | Prutchi ....................... 600/547 |
| 6,385,491 B1 | 5/2002 | Lindemans et al. |
| 6,387,369 B1 | 5/2002 | Pittenger et al. ............ 424/93.7 |
| 6,398,728 B1 | 6/2002 | Bardy ........................ 600/300 |
| 6,399,300 B1 | 6/2002 | Field ............................ 435/6 |
| 6,410,236 B1 | 6/2002 | Metzger ........................ 435/6 |
| 6,411,840 B1 | 6/2002 | Bardy ........................ 600/513 |
| 6,411,844 B1 | 6/2002 | Kroll et al. ..................... 607/5 |
| 6,424,847 B1 | 7/2002 | Mastrototaro et al. ........ 600/316 |
| 6,428,802 B1 | 8/2002 | Atala |
| 6,436,907 B1 | 8/2002 | Leiden et al. ................ 514/44 |
| 6,438,419 B1 | 8/2002 | Callaway et al. ............... 607/5 |
| 6,440,066 B1 | 8/2002 | Bardy ........................ 600/300 |
| 6,442,413 B1 | 8/2002 | Silver ........................ 600/345 |
| 6,443,949 B2 | 9/2002 | Altman ........................ 606/41 |
| 6,451,594 B1 | 9/2002 | Chien et al. ................. 435/320 |
| 6,453,195 B1 | 9/2002 | Thompson ..................... 607/3 |
| 6,459,917 B1 | 10/2002 | Gowda et al. ................ 600/345 |
| 6,459,929 B1 | 10/2002 | Hopper et al. ............... 600/513 |
| 6,463,335 B1 | 10/2002 | Munch et al. |
| 6,468,263 B1 | 10/2002 | Fischell et al. ........... 604/890.1 |
| 6,473,640 B1 | 10/2002 | Erlebacher ................... 600/547 |
| 6,475,232 B1 | 11/2002 | Babbs et al. |
| 6,478,737 B2 | 11/2002 | Bardy ........................ 600/301 |
| 6,501,983 B1 | 12/2002 | Natarajan et al. ........... 600/517 |
| 6,507,756 B1 * | 1/2003 | Heynen et al. .................. 607/9 |
| 6,511,477 B2 | 1/2003 | Altman et al. ................. 606/41 |
| 6,518,245 B1 | 2/2003 | Anderson et al. ............. 514/14 |
| 6,539,256 B1 | 3/2003 | KenKnight et al. ............. 607/5 |
| 6,540,725 B1 | 4/2003 | Ponzi |
| 6,541,116 B2 | 4/2003 | Michal et al. |
| 6,574,507 B1 * | 6/2003 | Bonnet ........................ 607/20 |
| 6,575,931 B1 | 6/2003 | Ponzi |
| 6,592,623 B1 | 7/2003 | Bowlin et al. |
| 6,604,000 B2 | 8/2003 | Lu .............................. 607/17 |
| 6,623,473 B1 | 9/2003 | Ponzi |
| 6,623,474 B1 | 9/2003 | Ponzi |
| 6,653,291 B1 | 11/2003 | Badylak et al. |
| 6,656,517 B2 | 12/2003 | Michal et al. |
| 6,671,558 B1 | 12/2003 | Soykan et al. |
| 6,689,117 B2 | 2/2004 | Sweeney et al. ............. 604/503 |
| 6,690,970 B1 | 2/2004 | Taheri et al. |
| 6,702,777 B2 | 3/2004 | Haim et al. |
| 6,733,996 B2 | 5/2004 | Froehlich et al. |
| 6,735,471 B2 | 5/2004 | Hill et al. |
| 6,748,653 B2 | 6/2004 | Lindemans et al. |
| 6,759,236 B1 | 7/2004 | Fung et al. |

| Patent Number | Date | Inventor |
|---|---|---|
| 6,775,574 B1 | 8/2004 | Soykan et al. |
| 6,801,805 B2 | 10/2004 | Stokes et al. |
| 6,810,286 B2 | 10/2004 | Donovan et al. |
| 6,832,112 B1 * | 12/2004 | Bornzin ............... 607/9 |
| 6,855,124 B1 | 2/2005 | Gonzalez et al. |
| 6,865,420 B1 | 3/2005 | Kroll |
| 6,902,522 B1 | 6/2005 | Walsh et al. |
| 6,905,476 B2 | 6/2005 | Ponzi |
| 6,919,207 B2 | 7/2005 | Goodman et al. |
| 6,965,798 B2 | 11/2005 | Kim |
| 6,973,349 B2 | 12/2005 | Salo |
| 7,039,462 B2 | 5/2006 | Pastore et al. |
| 2001/0000802 A1 | 5/2001 | Soykan et al. ............ 623/1.13 |
| 2001/0016193 A1 | 8/2001 | Engler ............... 424/93.21 |
| 2001/0051148 A1 | 12/2001 | Tremblay ............... 424/93.1 |
| 2001/0055590 A1 | 12/2001 | Kurachi ............... 424/93.21 |
| 2002/0001577 A1 | 1/2002 | Haverich et al. ......... 424/93.7 |
| 2002/0010492 A1 | 1/2002 | Donovan et al. |
| 2002/0012657 A1 | 1/2002 | Tremblay ............... 424/93.2 |
| 2002/0019350 A1 | 2/2002 | Levine et al. |
| 2002/0022259 A1 | 2/2002 | Lee et al. ............... 435/226 |
| 2002/0026228 A1 | 2/2002 | Schauerte ............... 607/122 |
| 2002/0031501 A1 | 3/2002 | Law ............... 424/93.1 |
| 2002/0031827 A1 | 3/2002 | Kanno et al. ............ 435/446 |
| 2002/0048800 A1 | 4/2002 | Gu et al. ............... 435/183 |
| 2002/0049154 A1 | 4/2002 | Grissom et al. |
| 2002/0055530 A1 | 5/2002 | Neuberger et al. ......... 514/381 |
| 2002/0065243 A1 | 5/2002 | Fung et al. |
| 2002/0072785 A1 | 6/2002 | Nelson et al. |
| 2002/0077311 A1 | 6/2002 | Leiden et al. ............ 514/44 |
| 2002/0098167 A1 | 7/2002 | Anversa et al. ........... 424/93.7 |
| 2002/0107553 A1 | 8/2002 | Hill et al. |
| 2002/0110910 A1 | 8/2002 | Gwathmey et al. ......... 435/325 |
| 2002/0115208 A1 | 8/2002 | Mitchell et al. |
| 2002/0124855 A1 | 9/2002 | Chachques ............... 128/898 |
| 2002/0127210 A1 | 9/2002 | Mickle et al. ............ 424/93.21 |
| 2002/0133198 A1 | 9/2002 | Kramer et al. ............ 607/9 |
| 2002/0142457 A1 | 10/2002 | Umezawa et al. ......... 435/366 |
| 2002/0147172 A1 | 10/2002 | Podsakoff et al. ......... 514/44 |
| 2002/0155101 A1 | 10/2002 | Donahue et al. |
| 2002/0161410 A1 | 10/2002 | Kramer et al. |
| 2002/0172663 A1 | 11/2002 | Palasis |
| 2002/0183686 A1 | 12/2002 | Darvish et al. |
| 2002/0183720 A1 | 12/2002 | Hill et al. |
| 2003/0004403 A1 | 1/2003 | Drinan et al. ............ 600/301 |
| 2003/0036773 A1 | 2/2003 | Whitehurst et al. |
| 2003/0040777 A1 | 2/2003 | Shemer et al. |
| 2003/0044802 A1 | 3/2003 | Sayler et al. |
| 2003/0059463 A1 | 3/2003 | Lahtinen |
| 2003/0060854 A1 | 3/2003 | Zhu ............... 607/25 |
| 2003/0065379 A1 | 4/2003 | Babbs et al. |
| 2003/0073235 A1 | 4/2003 | Lagarias et al. |
| 2003/0082148 A1 | 5/2003 | Ludwig et al. |
| 2003/0087867 A1 | 5/2003 | Vogels et al. |
| 2003/0104568 A1 | 6/2003 | Lee |
| 2003/0113303 A1 | 6/2003 | Schwartz |
| 2003/0125615 A1 | 7/2003 | Schwartz |
| 2003/0129750 A1 | 7/2003 | Schwartz |
| 2003/0130581 A1 | 7/2003 | Salo et al. |
| 2003/0148968 A1 | 8/2003 | Hammond et al. |
| 2003/0153952 A1 | 8/2003 | Auricchio et al. |
| 2003/0167081 A1 | 9/2003 | Zhu et al. |
| 2003/0171723 A1 | 9/2003 | Ponzi |
| 2003/0187396 A1 | 10/2003 | Ponzi |
| 2003/0187490 A1 | 10/2003 | Gliner |
| 2003/0195470 A1 | 10/2003 | Ponzi |
| 2003/0204206 A1 | 10/2003 | Padua et al. |
| 2003/0211130 A1 | 11/2003 | Sanders et al. |
| 2003/0216811 A1 | 11/2003 | Badylak |
| 2003/0216812 A1 | 11/2003 | Badylak |
| 2004/0002739 A1 | 1/2004 | Cates et al. ............ 607/6 |
| 2004/0006395 A1 | 1/2004 | Badylak |
| 2004/0018174 A1 | 1/2004 | Palasis |
| 2004/0030379 A1 | 2/2004 | Hamm et al. |
| 2004/0038400 A1 | 2/2004 | Froehlich et al. |
| 2004/0043006 A1 | 3/2004 | Badylak et al. |
| 2004/0047909 A1 | 3/2004 | Ragheb et al. |
| 2004/0048286 A1 | 3/2004 | Lee |
| 2004/0087019 A1 | 5/2004 | Soykan et al. |
| 2004/0098075 A1 | 5/2004 | Lee |
| 2004/0106954 A1 | 6/2004 | Whitehurst et al. |
| 2004/0131601 A1 | 7/2004 | Epstein et al. |
| 2004/0132184 A1 | 7/2004 | Dennis et al. |
| 2004/0158289 A1 | 8/2004 | Girouard et al. |
| 2004/0158290 A1 | 8/2004 | Girouard et al. |
| 2004/0161421 A1 | 8/2004 | Komowski et al. |
| 2004/0186546 A1 | 9/2004 | Mandrusov et al. |
| 2004/0208845 A1 | 10/2004 | Michal et al. |
| 2004/0213770 A1 | 10/2004 | Seward et al. |
| 2004/0214182 A1 | 10/2004 | Sharma et al. |
| 2004/0215251 A1 | 10/2004 | Sharma et al. |
| 2004/0215253 A1 | 10/2004 | Weinberg |
| 2004/0253209 A1 | 12/2004 | Soykan et al. |
| 2005/0002912 A1 | 1/2005 | Chachques |
| 2005/0005923 A1 | 1/2005 | Herrin |
| 2005/0008628 A1 | 1/2005 | Feld et al. |
| 2005/0013870 A1 | 1/2005 | Freyman et al. |
| 2005/0021091 A1 | 1/2005 | Laske et al. |
| 2005/0025752 A1 | 2/2005 | Kutryk et al. |
| 2005/0059153 A1 | 3/2005 | George et al. |
| 2005/0059999 A1 | 3/2005 | Mongeon et al. |
| 2005/0096701 A1 | 5/2005 | Donovan et al. |
| 2005/0112759 A1 | 5/2005 | Radisic et al. |
| 2005/0118144 A1 | 6/2005 | Zhang |
| 2005/0130136 A1 | 6/2005 | Lee |
| 2005/0137626 A1 | 6/2005 | Pastore et al. |
| 2005/0137671 A1 | 6/2005 | Liu et al. |
| 2005/0192637 A1 | 9/2005 | Girouard et al. |
| 2005/0245972 A1 | 11/2005 | Onyekaba et al. |
| 2005/0283197 A1 | 12/2005 | Daum et al. |
| 2006/0008500 A1 | 1/2006 | Chavan et al. |
| 2006/0134071 A1 | 6/2006 | Ross et al. |
| 2006/0134079 A1 | 6/2006 | Sih et al. |
| 2006/0136027 A1 | 6/2006 | Westlund et al. |
| 2006/0136028 A1 | 6/2006 | Ross et al. |
| 2007/0027487 A1 | 2/2007 | Mika et al. |

FOREIGN PATENT DOCUMENTS

| | | |
|---|---|---|
| EP | 0347708 | 12/1989 |
| EP | 0467695 A2 | 1/1992 |
| EP | 0545628 A2 | 6/1993 |
| EP | 0550343 | 7/1993 |
| EP | 0550344 | 7/1993 |
| EP | 0620420 | 10/1994 |
| EP | 633031 A1 | 1/1995 |
| EP | 0674916 | 10/1995 |
| EP | 1050265 | 11/2000 |
| EP | 1142607 A2 | 10/2001 |
| WO | WO-93/20888 | 10/1993 |
| WO | WO-96/32984 | 10/1996 |
| WO | WO-96/40195 | 12/1996 |
| WO | WO-97/06854 | 2/1997 |
| WO | WO-97/33513 | 9/1997 |
| WO | WO-98/02150 A1 | 1/1998 |
| WO | WO-98/15317 A1 | 4/1998 |
| WO | WO-98/34537 A1 | 8/1998 |
| WO | WO-9925385 A1 | 5/1999 |
| WO | WO-00/07497 A1 | 2/2000 |
| WO | WO-00/17326 | 3/2000 |
| WO | WO-00/27466 A1 | 5/2000 |
| WO | WO-00/54661 A1 | 9/2000 |
| WO | WO-00/74584 A1 | 12/2000 |
| WO | WO-01/03750 A1 | 1/2001 |
| WO | WO-02/04063 A1 | 1/2002 |
| WO | WO-02/05866 A2 | 1/2002 |

| | | |
|---|---|---|
| WO | WO-02/49669 A2 | 6/2002 |
| WO | WO-0249714 A2 | 6/2002 |
| WO | WO-02/070065 A2 | 9/2002 |
| WO | WO-2004016200 | 2/2004 |
| WO | WO-2004/024206 A1 | 3/2004 |
| WO | WO 2004/030706 | 4/2004 |
| WO | WO-2004/030706 A2 | 4/2004 |
| WO | WO-2004050180 A2 | 6/2004 |
| WO | WO-2004080533 A1 | 9/2004 |
| WO | WO-2004093969 A1 | 11/2004 |
| WO | WO-2005084751 A2 | 9/2005 |
| WO | WO-2005084751 A3 | 9/2005 |

OTHER PUBLICATIONS

Daum, Douglas R., "Systems and Methods for Hypotension", U.S. Appl. No. 11/141,260, filed May 31, 2005, 279.968us1, 51 pages.

Pastore, Joseph M., et al., "Method and Apparatus for Device Controlled Gene Expression for Cardiac Protection", U.S. Appl. No. 11/220,397, filed Sep. 6, 2005, 68 Pgs.

Patberg, Kornelis W., "Cardiac Memory Is Associated With Decreased Levels of the Transcriptional Factor CREB Modulated by Angiotensin II and Calcium", *Circulation Research*, vol. 91 (2003),472-478.

Zou, Y. , et al., "Heat Shock Transcription Factor 1 Protects Cardiomyocytes From Ischemia/Reperfusion Injury", *Circulation*, 108 (24) ISSN: 1524-4539 XP002345863,(Dec. 16, 2003),3024-3030.

Allman, A. J., et al., "Xenogeneic Extracellular Matrix Grafts Elicit a TH2-Restricted Immune Response", *Transplantation*, 71(11), (2001), 1631-40.

Badylak, S., et al., "Extracellular Matrix for Myocardial Repair", *Heart Surgery Forum*, 6(2), (2003), E20-E26.

Badylak, S. F., et al., "Marrow-Derived Cells Populate Scaffolds Composed of Xenogeneic Extracellular Matrix", *Experimental Hematology*, 29(11), (2001), 1310-8.

Badylak, S. F., et al., "Resorbable Bioscaffold for Esophageal Repair in a Dog Model", *Journal of Pediatric Surgery*, 35(7), (2000), 1097-1103.

Badylak, Stephen F., "The Extracellular Matrix as a Scaffold for Tissue Reconstruction", *Seminars in Cell Developmental Biology*, 13(5), ( 2002), 377-383.

Burton, D. Y., et al., "The Incorporation of an Ion Channel Gene Mutation Associated with the Long QT Syndrome (Q9E-hMiRPI) in a Plasmid Vector for Site-Specific Arrhythmia Gene Therapy: In Vitro and In Vivo Feasibility Studies", *Human Gene Therapy*, 14, (2003) , 907-922.

Del Monte, F. , et al., "Targeting Calcium Cycling Proteins in Heart Failure Through Gene Transfer", *The Journal of Physiology*, 546(1), (2002), 49-61.

Donahue, J. K., et al., "Focal Modification of Electrical Conduction in the Heart by Viral Gene Transfer", *Nature Medicine*, 6(12), (2000),1395-1398.

Gabouev, A I., et al., "In vitro Construction of Urinary Bladder Wall Using Porcine Primary Cells Reseeded on Acellularized Bladder Matrix and Small Intestinal Submucosa", *The International Journal of Artifical Organs*, 26(10), (2003), 935-942.

Girouard, S. D., et al., "Method and Apparatus for Device Controlled Gene Expression", U.S. Appl. No. 10/788,906, filed Feb. 27, 2004, 80 Pages.

Girouard, S. D., "Method and Apparatus to Modulate Cellular Regeneration Post Myocardial Infarct", U.S. Appl. No. 10/862,716, filed Jun. 7, 2004, 71 Pages.

Hamawy, A. H., et al., "Cardiac Angiogenesis and Gene Therapy: A Strategy for Myocardial Revascularization", *Current Opinion in Cardiology*, 14, (1999), 515-522.

Hodde, Jason P., et al., "Retention of Endothelial Cell Adherence to Porcine-Derived Extracellular Matrix After Disinfection and Sterilization", *Tissue Engineering*, 8(2), (Apr. 2002), 225-34.

Hong, Y. S., et al., "Localized Immunosuppression in the Cardia Allograft Induced by a New Liposome-Mediated IL-10 Gene Therapy", *J. Heart Lung Transplant*, 21, (2002), 1188-1200.

Huq, F., et al., "Session 5: Cellular and Subcellular Basis of Remodeling—Modulating Signalling Pathways in Hypertrophy and Heart Failure by Gene Transfer", *Journal of Cardiac Failure*, 8(6)(Suopl.), (2002), S389-S400.

Ingber, D. E., "Mechanical signaling and the cellular response to extracellular matrix in angiogenesis and cardiovascular physiology", *Circulation Research*, 91(10), (2002), 877-887.

Jayakumar, MD, J., et al., "Gene Therapy for Myocardial Prevention—Transfection of Donor Hearts With Heat Shock Protein 70 Gene Protects Cardiac Function Against Ischemia-Reperfusion Therapy", *Circulation*, 102 (*Suppl. III*), (2000), III-302-III-306.

Koch, W. J., et al., "Gene Transfer of β-Adrenergic Signalling Components for Heart Failure", *Journal of Cardiac Failure*, 8(6) (Suppl.), (2002), S526-S531.

Kozarsky, K. F., "Gene Therapy for Cardiovascular Disease", *Current Opinion in Pharmacology*, 1, (2001), 197-202.

Krum, Henry, "New and Emerging Pharmacological Strategies in the Management of Chronic Heart Failure", *Current Opinion in Pharmacology*, 1(2), (Apr. 2001), 126-133.

Lee, L. Y., et al., "Exogenous Control of Cardiac Gene Therapy: Evidence of Regulated Myocardial Transgene Expression After Adenovirus and Adeno-Associated Virus Transfer of Expression Cassettes Containing Corticosteroid Response Element Promoters", *J Thorac Cardiovasc Surg*, 118, (1999), 26-35.

Lin, H. , Specific Region of the c-*myc* Promoter is Responsive to Electric and Magnetic Fields, *Journal of Cellular Biochemistry*, 54, (1994), 281-288.

Lin, H. , "Regulating Genes with Electromagnetic Response Elements", *Journal of Cellular Biochemistry*, 81, (2001),143-148.

MacNeill, Md, B. D., et al., "Targeting Signaling Pathways in Heart Failure by Gene Transfer", *Current Atherosclerosis Reports*, 5, (2003),178-185.

Marbán, E. , et al., "Gene Therapy for Cardiac Arrhythmias", *Cold Spring Harbor Symposia on Quantitative Biology, vol. LXVII—The Cardiovascular System*, Published by Cold Spring Harbor Laboratory Press,(2002),527-531.

McPherson, T B., et al., "Galaα(1,3)Gal Epitope in Porcine Small Intestinal Submucosa", *Tissue Engineering*, 6(3), (Jun. 2000), 133139.

Meezan, E., et al., "A Simple, Versatile, Nondisruptive Method for the Isolation of Morphologically and Chemicaly Pure Basement Membranes From Several Tissues", *Life Sciences*,17(11), (1974), 1721-1732.

Michal, E. T., et al., "Methods and Compositions to Treat Myocardiac Conditions", U.S. Appl. No. 10/802,955, filed Mar. 16, 2004, 113 pgs.

Nuss, H. B., et al., "Reversal of Potassium Channel Deficiency in Cells from Failing Hearts by Adenoviral Gene Transfer: A Prototype for Gene Therapy for Disorders of Cardiac Excitability and Contractility", *Gene Therapy*, 3, (1996), 900-912.

Radisic, M , "From the Cover: Functional Assembly of Engineered Myocardium by Electrical Stimulation of Cardiac Myocytes Cultured on Scaffolds", *Proc Natl Acad Sci U S A.*, 101(52), (2004), 18129-18134.

Ross, J. , "Epicardial Patch Including Isolated Extracellular Matrix With Pacing Electrodes", U.S. Appl. No. 11/017,627, filed Dec. 20, 2004, 87 pgs.

Ross, J., et al., "Use of Extracellular Matrix and Electrical Therapy", U.S. Appl. No. 11/017,237, filed Dec. 20. 2004, 89 pgs.

Rubenstrunk, A., et al., "Transcriptional Activation of the Metallothionein I Gene by Electric Pulses in vivo: Basis for the Development of a New Gene Switch System", *The Journal of Gene Medicine*, 5, (2003), 773-783.

Rutanen, J., et al., "Progress and Prospects—Post-Intervention Vessel Remodeling", *Gene Therapy*, 9, (2002),1487-1491.

Sarikaya, A., et al., "Antimicrobial Activity Associated With Extracellular Matrices", *Tissue Engineering*, 8(1), (2002), 63-71.

Shimizu, T., et al., "Cell Sheet Engineering for Myocardial Tissue Reconstruction", *Biomaterials*. 24(13), (Jun. 2003),2309-2316.

Shin, H., et al., "Biomimetic materials for tissue engineering", *Biomaterials*, 24(24), (2003), 4353-4364.

Sih, H. J., "Implantable Medical Devices Comprising Isolated Extracellular Matrix", U.S. Appl. No. 11/017,432, filed Dec. 20, 2004, 87 pgs.

Stock, U. A., et al., "Tissue Engineering: Current State and Prospects", *Annu. Rev Med.*, 52, (2001), 443-451.

Tran, N., et al., "Autologous Cell Transplantation and Cardiac Tissue Engineering: Potential Applications in Heart Failure", *Biorheology*, 40(1-3), (2003), 411-415.

Walther, W., et al., "Cell Type Specific and Inducible Promoters for Vectors in Gene Therapy as an Approach for Cell Targeting", *Journal of Molecular Medicine*, 74, (1996),379-392.

Wattanapitayakul, S. K., et al., "Recent Developments in Gene Therapy for Cardiac Disease", *Biomedical & Pharmacotherapy*, 54, (2000),487-504.

Westlund, Randy, "Lead Electrode Incorporating Extracellular Matrix", U.S. Appl. No. 11/017,238, filed Dec. 20, 2004, 85 pgs.

Wyman, T., et al., "Promoter-Activated Expression of Nerve Growth Factor for Treatment of Neurodegenerative Diseases", *Gene Therapy*, 6, (1999),1648-1660.

Zhu, F., et al., "Purification, Characterization and Evaluation of Antibacterial Peptide from Resorbable Tissue Scaffold", *Abstracts of Papers American Chemical Society*, 224(1-2), (Abstract No. BIOT 137), (2002), 3 pgs.

Arnaud, Claire, et al., "iNOS is a mediator of the heat stress-induced preconditioning against myocardial infarction in vivo in the rat", *Cardiovascular Research*, 58, (2003), 118-125.

Askari, Arman T., et al., "Targeted Gene Therapy for the Treatment of Cardiac Dysfunction", *Seminars in Thoracic and Cardiovascular Surgery*, vol. 14, No. 2., (Apr. 2002),pp. 167-177.

Bardone, Alessandro, et al., "Comparison of Right and Left Ventricular Responses to Left Ventricular Assist Device Support in Patients with Severe Heart Failure: A Primary Role of Mechanical Unloading Underlying Reverse Remodeling", *Circulation,*, (2001),pp. 670-675.

Boheler, Kenneth R., et al., "Differentiation of Pluripotent Embryonic Stem Cells into Cardiomyocytes", *Circ Res.*, vol. 91,, (2002),pp. 189-201.

Brunner, Friedrich, et al., "Attenuation of myocardial ischemia/reperfusion injury in mice with myocyte-specific overexpression of endothelial nitric oxide synthase", *Cardiovascular Research*, 57, (2003),55-62.

Condorelli, G, et al., "Cardiomyocytes Induce Endothelial Cells to Trans-Differentiate into Cardiac Muscle: Implications for Myocardium Regeneration", *Proc Natl Acad Sci.*, vol. 98, No. 19,, (Sep. 11, 2001),pp. 10733-10738.

Depre, Christophe, et al., "Metabolic Aspects of Programmed Cell Survival and Cell Death in The Heart", *Cardiovascular Research* vol. 45,, (2000),pp.538-548.

Ferdinandy, Peter, et al., "Nitric oxide, superoxide, and peroxynitrite in myocardial ischaemia-reperfusion injury and preconditioning", *British Journal of Pharmacology*, vol. 138, No. 4, (2003),532-543.

Flogel, Ulrich, et al., "Myoglobin: A scanvenger of bioactive NO", *PNAS*, vol. 98, No. 2,(Jan. 16, 2001),735-740.

Freedman, Saul B., et al., "Therapeutic Angiogenesis for Ischemic Cardiovascular Disease", *J. Mol Cell Cardiol.*, vol. 33,, (2001),pp. 379-393.

Gewaltig, Michael T., et al., "Vasoprotection ny nitric oxide: mechanisms and therapeutic potential", *Cardiovascular Research*, 55, (Feb. 14, 2002) ,250-260.

Graham, Regina M., et al., "Gene and Cell Therapy for Heart Disease", *IUBMB Life*, vol. 54,, (2002),pp. 59-66.

Hada, Yoshiyuki, et al., "Pulsus alternans determined by biventricular simultaneous systolic time intervals", *Circulation*, vol. 65, No. 3, (Mar. 1982),617-26.

Hakuno, Daihiko, et al., "Bone Marrow-Derived Regenerated Cardiomyocytes (CMG Cells) Express Functional Adrenergic and Muscarinic Receptors", *Circulation*; 105,, (2002),pp. 380-386.

Harjai, Kishore J., et al., "Therapeutic Angiogenesis: a Fantastic New Adventure", *Journal of Interventional Cardiology*, vol. 15, No. 3., (2002),pp. 223-229.

Heerdt, Paul M., et al., "Chronic Unloading By Left Ventricular Assist Device Reverses Contractile Dysfunction and Alters Gene Expression in End-Stage Heart Failure", *Circulation*, 102,, (2000),pp. 2713-2719.

Hsia, Peng W., et al., "Absolute Depolarization Vector Characteristics Associated with Successful Defibrillation: Evidence of a Vulnerable Period During Ventricular Fibrillation", *Circulation*, 82 (4), Supplement III, Abstracts, Abstract No. 2933,(Oct. 1990),III-738.

Hsia, Peng W., et al., "Genesis of SIgmoidal Dose-Response Curve During Defibrillation by Random Shock: A Theoretical Model Based on Experimental Evidence for a Vulnerable Window During Ventricular Fibrillation", *Pace*, 13, NASPE Young Investigator Awardee-1990,(Oct. 1990),pp. 1326-1342.

Hsia, Peng W., et al., "Improved Nonthoractomy Defibrillation Based on Ventricular Fibrillation Waveform Characteristics", *Pace, 18—NASPE Abstracts*, Abstract No. 29,(Apr. 1995),p. 803.

Hsu, William, et al., "Effect of Shock Timing on Defibrillation Success", *Pace*, 20, Part II,(1997),pp. 153-157.

Isner, Jeffrey M., "Myocardial Gene Therapy", *Nature*, vol. 415, (Jan. 10, 2002).

Jackson, Kathyjo A., et al., "Regeneration of Ischemic Cardiac Muscle and Vascular Endothelium By Adult Stem Cells", *The Journal of Clinical Investigation*, vol. 107, No. 11,, (Jun. 2001),pp. 1395-1402.

Jain, Mohit, et al., "Cell Therapy Attenuates Deleterious Ventricular Remodeling and Improves Cardiac Performance After Myocardial Infarction", *Circulation,*, (2001),pp. 1920-1927.

Jones, Douglas L., et al., "Ventricular Fibrillation: The Importance of Being Coarse?", *Journal of Electrocardiology*, 17 (4), (1984),pp. 393-399.

Kehat, Izhak, et al., "Human Embryonic stem Cells Can Differentiate into Myocytes with Structural and Functional Properties of Cardiomyocytes", *The Journal of Clinical Investigation*, vol. 108, No. 3,, (Aug. 2001),pp. 363-364.

Kocher, A A., et al., "Neovascularization of Ischemic Myocardium by Human Bone-Marrow-Derived Angioblasts Prevents Cardiomyocyte Apoptosis, Reduces Remodeling and Improves Cardiac Function", *Nature Medicine*, vol. 7, No. 4,, (Apr. 2001),pp. 430-436.

Komuro, Issei, et al., "Control of Cardiac Gene Expression by Mechanical Stress", *Annu Rev Physiol.,*, (1993),pp. 55-75.

Konta, Tsuyoshi, et al., "Significance of Discordant ST Alternans in Ventricular Fibrillation", *Circulation*, vol. 82. No. 6, Dec. 1990, American Heart Association,(1990),2185-2189.

Kuelz, Kathy W., et al., "Integration of Absolute Ventricular Fibrillation Voltage Correlates with Successful Defibrillation", *IEEE Transactions on Biomedical Engineering*, 41 (8), (Aug. 1994),pp. 782-791.

Laham, Roger J., et al., "Gene Transfer to Induce Angiogenesis in Myocardial and Limb Ischaemia", *Expert Opin Biol Ther.*, 1(6),, (2001),pp. 985-994.

Lee, Y. C., et al., "Pulsus alternans in patients with congestive cardiomyopathy", *Circulation*, vol. 65, No. 7, (Jun. 1982),1533-4.

Li, Qianghong, et al., "Gene Therapy With Inducible Nitric Oxide Synthase Protects Against Myocardial Infarction via a Cyclooxygenase-2-Dependent Mechanism", *Circulation Research*, 92, (2003),741-748.

Lodie, Tracey A., et al., "Systematic Analysis of Reportedly Distinct Populations of Multipotent Bone Marrow-Derived Stem Cells Reveals a Lack of Distinction", *Tissue Engineering*, vol. 8, No. 5,, (2002),pp. 739-751.

Losordo, Douglas W., et al., "Gene Therapy for Myocardial Angiogenesis", *Am Heart J.*, vol. 138,, (1999),pp. S132-S141.

Lovett, Eric G., "Technique for Discriminating Between Coordinated and Uncoordinated Cardiac Rhythms", U.S. Appl. No. 10/435,487, filed May 9, 2003, SLWK, assigned to Cardiac Pacemakers, Inc. ,(May 9, 2003),36 pgs.

Luepker, R. V., et al., "Transthoracic Electrical Impedance: Quantitative Evaluation of a Non-Invasive Measure of Thoracic Fluid Volume", *American Heart Journal*, vol. 85, No. 1,(Jan. 1973),83-93.

Mai, J., et al., "Enhanced Rate Response Algorithm for Orthostatic Compensation Pacing", *Pace*, 23, NASPE Abstracts, Abstract No. 678,(Apr. 2000),p. 722.

Mann, Brenda K., et al., "Tissue Engineering in the Cardiovascular System: Progress Toward a Tissue Engineered Heart", *Anat Rec.* 263,, (2001),pp. 367-371.

Menasche, Philippe, "Cell Therapy of Heart Failure", *CR Biologies*, vol. 325,, (2002),pp. 731-738.

Min, Mart, et al., "Electrical Impedance and Cardiac Monitoring-Technology, Potential and Applications", *International Journal of Bioelectromagnetism*, 5, (2003),53-56.

Miyagawa, Shigeru, et al., "Myocardial Regeneration Therapy for Heart Failure: Hepatocyte Growth Factor Enhances the Effect of Cellular Cardiomyoplasty", *Circulation*, vol. 105,, (2002),pp. 2556-2561.

Mower, Morton M., et al., "Synchronization of Low-Energy Pulses to Rapid Deflection Signals as a Possible Mechanism of Subthreshold Ventricular Defibrillation", *Abstracts of the 55th Scientific Sessions*, Abstract No. 298,(1982),p. II-75.

Nemer, Georges, et al., "Regulation of Heart Development and Function Through Combinatorial Interactions of Transcription Factors" *The Finnish Medical Society Duodecim, Ann Med*, vol. 33,, (2001),pp. 604-610.

Orlic, Donald, et al., "Bone Marrow Cells Regenerate Infarcted Myocardium", *Nature*, vol. 410., (Apr. 5, 2001),pp. 701-705.

Ostadal, Petr, et al., "The effect of early treatment by cerivastatin on the serum level of C-reactive protein, interleukin-6, and interleukin-8 in patients with unstable angina and non-Q-wave myocardial infarction", *Molecular and Cellular Biochemistry*, 246, (2003),45-50.

Paolocci, Nazareno, et al., "Positive inotropic and lusitropic effects of HNO/NO- in failing hearts: Independence from beta-adrenergic signaling", *Proceedings of the National Academy of Sciences*, vol. 100, No. 9, (Apr. 29, 2003),5537-5542.

Pastore, Joseph M., "Method And Apparatus for Modulating Cellular Metabolism During Post-Ischemia Or Heart Failure", U.S. Appl. No. 10/645,823, filed Aug. 21, 1003, 46 pages.

Pasumarthi, Kishore B., et al., "Cardiomyocyte Cell Cycle Regulation" *Circ Res.*, vol. 90,, (2002),pp. 1044-1054.

Pimentel, Rhea C., et al., "Autocrine Regulation of Myocyte C×43 Expression by VEGF", *Circ Res.*, 90:, (2002),pp. 671-677.

Pouzet, Bruno, et al., "Intramyocardial Transplantation of Autologous Myoblasts: Can Tissue Processing Be Optimized?", *Circulation*, vol. 102,,(2000),pp. III-210III-215.

Prinzen, Frits W., et al., "Mapping of Regional Myocardial Strain and Work During Ventricular Pacing: Experimental Study Using Magnetic Resonance Imaging Tagging", *Journal of American College of Cardiology*, vol. 33, No. 6,,(1999),pp. 1735-1742.

Reinecke, Hans, et al., "Survival, Integration, and Differentiation of Cardiomyocyte Grafts: a Study in Normal and Injured Rat Hearts", *Circulation*,,(1999),pp. 193-202.

Robbins, Jeffrey, "Remodeling the Cardiac Sarcomere Using Transgenesis", *Annu Rev Physiol.*, vol. 62, (2000),pp. 261-287.

Rosborough, John P., et al., "Electrical Therapy for Pulseless Electrical Activity", NASPE, Apr. 2000, v. 23, No. 4 Part II,, Abstract, (2000),591.

Rubenstein, Donald S., et al., "Premature Beats Elicit a Phase Reversal of Mechanoelectrical Alternans in Cat Ventricular Myocytes", *Circulation*, vol. 91, No. 1, Jan. 1995, American Heart Association,(Jan. 1, 1995),201-214.

Salloum, Fadi, et al., "Sildenafil Induces Delayed Preconditioning Through Inducible Nitric Oxide Synthase-Dependent Pathway in Mouse Heart", *Circulation Research*, 92, (Apr. 2003),595-597.

Schaefer, Saul, et al., "Clinical and hemodynamic characteristics of patients with inducible pulsus alternans", *American Heart Journal*, vol. 115, No. 6, (Jun. 1988), 1251-7.

Smith, Damon, et al., "Influence of the Aortic Component of the Second Heart Sound on Left Ventricular Maximal Negative dP/dt in the Dog", *Am. J. Cardiol.*,55: 205, (1985),205-209.

Suematsu, Yoshihiro, et al., "L-Arginine given after ischaemic preconditioning can enhance cardioprotection in isolated rat hearts", *European Journal of Cardio-thoracic Surgery*, 19, (2001),873-879.

Suzuki, Ken, et al., "Cell Transplantation for the Treatment of Acute Myocardial Infarction Using Vascular Endothelial Growth Factor-Expressing Skeletal Myoblasts", *Circulation*; 104[suppl I],, (2001),pp. I207-I212.

Taylor, Doris A., et al., "Regenerating Functional Myocardium: Improved Performance after Skeletal Myoblast Transplantation", *Nature Medicine*, vol. 4, No. 8,, (Aug. 1998),pp. 929-933.

Terracio, Louis, et al., "Effects of Cyclic Mechanical Stimulation of the Cellular Components of the Heart: In Vitro.", *In Vitro Celluллar & Develomental Biology*, vol. 24, No. 1,, (Jan. 1988),pp. 53-58.

Washizu, Masao, et al., "Handling Biological Cells Using a Fluid Integrated Circuit", *IEEE Transactionson Industry Applications*, vol. 26, No. 2, (Mar./Apr. 1990),pp. 352-358.

Wobus, Anna M., et al., "Embryonic Stem CellDerived Cardiac Differentiation: Modulation of Differentiation and "Loss-of-Function" Analysis In Vitro", *TCM.* vol. 8, No. 2, (1998),pp. 64-74.

Woldbaek, Per R., et al., "Increased cardiac IL-18 mRNA, pro-IL-18 and plasma IL-18 after myocardial infarction in the mouse; a potential role in cardiac dysfunction", *Cardiovascular Research*, 59, (2003),122-131.

Wolfrum, Sebastian, et al., "Acute Reduction of Myocardial Infarct Size By a Hydroxymethyl Glutaryl Coenzyme A Reductase Inhibitor Is Mediated By Endothelial Nitric Oxide Synthase", *J. Cardiovas Pharmacol*, vol. 41, No. 3, (Mar. 2003),474-480.

Wunderlich, Carsten, et al., "Acute Inhibition of Myoglobin Impairs Contractility and Energy State of iNOS-Overexpressing Hearts", *Circulation Research*, 92, (2003),1352-1358.

Xu, Chunhui, et al., "Characterization and Enrichment of Cardiomyocytes Derived from Human Embryonic Stem Cells", *Circ Res.*, vol. 91,, (2002),pp. 501-508.

Zhuang, Jianping, et al., "Pulsatile Stretch Remodels Cell-to-Cell Communication in Cultured Myocytes", *Circ Res.*, 87,, (2000),pp. 316-322.

Zimmermann, WH, et al., "Tissue Engineering of a Differentiated Cardiac Muscle Construct", *Circ Res.*, vol. 90,, (2002),pp. 223-230.

Cate, F. U., et al., "Endocardial and epicardial steorid lead pacing in the neonantal and paediatric age group", *Heart*, 88,www.heartlnl.com, (2002), 392-396.

Cohen, Mitchell I., et al., "Permanent Epicardial Pacing in Pediatric Patients", *Circulation*, 103, "http://www.circulationaha.org", (2001), 2585-2590.

Conley, B. J., et al., "Derivation, propagation and differentiation of human embryonic stem cells",*The International Journal of Biochemistry &Cell Biology*, 36, (2004), 555-567.

De Silva, R., et al., "Delivery and tracking of therapeutic cell preparations for clinical cardiovascular applications", *Cytotherapy*, 6(6), (2004), 608-614.

Eck, S., et al., "Gene-Based Therapy", *Goodman & Gilman's The Pharmacological Basis of Therapeutics, Chapter 5, Section 1, General Principles*, New York; McGraw-Hill, (2001), 77-101.

Gage, H. F., "Cell Therapy", *Nature*, 392, Supp., (Apr. 28, 1998), 18-24.

Kofidis, T., et al., "In vitro engineering of heart muscle: Artificial myocardial tissue", *The Journal of Thoracic and Cardiovascular Surgery*, 124 (1), (2002), 63-69.

Odorico, S. J., et al., "Multilineage Differentiation from Human Embryonic Stem Cell Lines", *Stem Cells*, 19; www.StemCells.com, (2001), 193-204.

Parikh, S., et al., "Endothelial Cell Delivery for Cardiovascular Therapy", *Advanced Drug Delivery Reviews*, 42, (2000), 139-161.

Pfeifer, A., et al., "Gene Therapy: Promises and Problems", *Ann. Rev. of Genomics and Hum. Genet.*, 2, (2001), 177-211.

Samstein, B., et al., "Physiologic and Immunologic Hurdles to Xenotransplantation", *Journal of the American Society of Nephrology*, 12, (2001), 182-193.

Srour, E. F., et al., "Ex Vivo Expansion of Hematopoietic Stem and Progenitor Cells: Are We There Yet?", *The Journal of Hematotherapy*, 8, (1999), 93-102.

Verma, I. M., et al., "Gene Therapy—Promises, Problems and Prospects", *Nature*, 389 (Sep. 18, 1997), 239-242.

Bursac, N., et al., "Cardiac Muscle Tissue Engineering: toward an in vitro Model Electrophysiological Studies", *Am. J. Physio.*; 277, Heart Cric, Physiol.; 46,(1999),H433-H444.

Gautam, A., et al., "Delivery Systems for Pulmonary Gene Therapy", *Am. J. Respir. Med.*, 1(1), (2002),35-46.

McCluskie, M. J., et al., "Route and Method of Delivery of DNA Vaccine Influence Immune Responses in Mice and Non-Human Primates", *Molecular Medicine*, 5, (1999), 287-300.

Rideout III, W. M., et al., "Nuclear Cloning and Epigenetic Reprogramming of the Genome", *Science*, 293, www.sciencemag.org, (Aug. 10, 2001), 1093-1098.

Stolen, Craig, et al., "Method and Apparatus for Preconditioning of Cells", U.S. Appl. No. 11/424,066, filed Jun. 14, 2006, 36 Pages.

"U.S. Appl. No. 10/862,716 Final Office Action mailed Jul. 13, 2007", 24 pgs.

"U.S. Appl. No. 10/862,716 Non Final Office Action mailed Sep. 19, 2007", 30 pgs.

"U.S. Appl. No. 10/862,716 Non Final Office Action mailed Dec. 14, 2006", 27 pgs.

"U.S. Appl. No. 10/862,716 Response filed Mar. 14, 2007 to Non Final Office Action mailed Dec. 14, 2006", 18 pgs.

"U.S. Appl. No. 10/862,716 Response filed Sep. 12, 2007 to Final Office Action mailed Jul. 13, 2007", 24 pgs.

U.S. Appl. No. 10/862,716, Response filed Dec. 19, 2007 to Non-Final Office Action mailed Sep. 19, 2007, 18 pgs.

Chachques, J. C., et al., "Electrostimulation Enhanced Fatigue Resistant Myosin Expression in Cellular Cardiomyoplasty", *Circulation*, 104(Suppl. 2), (Abstract No. 2626), Abstracts from Scientific Sessions 2001, Anaheim, CA, Nov. 11-14, 2001, (2001), II-555-II-556.

Pratt, A. B., et al., "Synthetic Extracellular Matrices for in Situ Tissue Engineering", *Biotechnology and Bioengineering*, 86(1), (2004), 27-36.

Shimizu, T., et al., "Electrically Communicating Three-Dimensional Cardiac Tissue Mimic Fabricated by Layered Cultured Cardiomyocyte Sheets", *J. Biomedical Materials Research*, 60, (2004), 110-117.

Willey, C. D., et al., "Focal Complex Formation in Adult Cardiomyocytes is Accompanied by the Activation of β3 Integrin and c-Src", *Journal of Molecular and Cellular Cardiology*, 35, (2003), 671-683.

Yao, M., et al., "Long-Term Outcome of Fetal Cell Transplantation on Postinfarction Ventricular Remodeling and Function", *Journal of Molecular and Cellular Cardiology*, 35, (2003), 661-670.

Zimmermann, W.-H., et al., "Engineered Heart Tissue for Regeneration of Diseased Hearts", *Biomaterials*, 25, (2004), 1639-1647.

"U.S. Appl. No. 10/862,716, Final Office Action mailed Aug. 20, 2008", 6 pgs.

"U.S. Appl. No. 10/862,716, Response filed Nov. 19, 2008 to Final Office Action mailed Aug. 20, 2008", 11 pgs.

US 6,875,206, 04/2005, Ponzi (withdrawn)

* cited by examiner

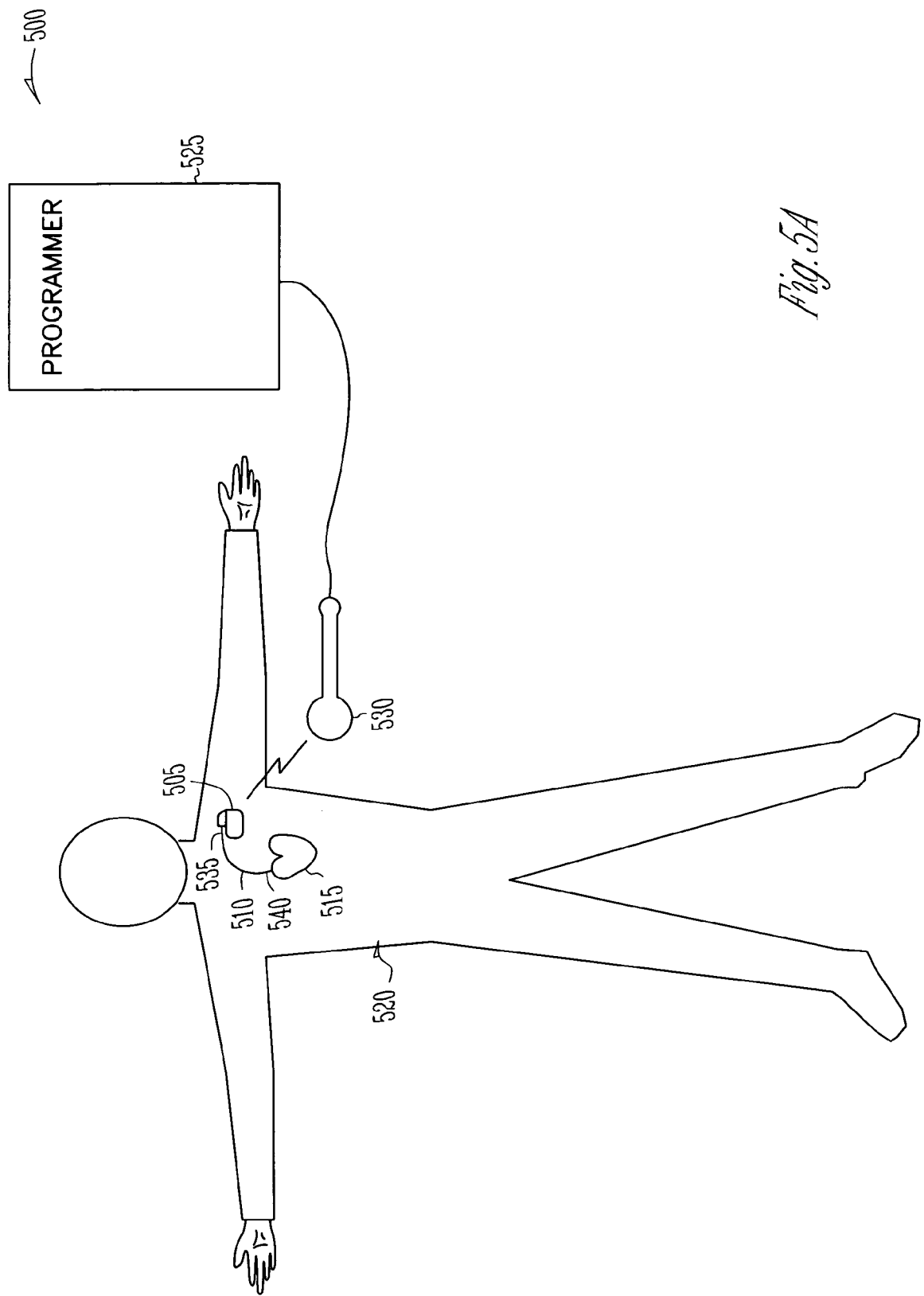

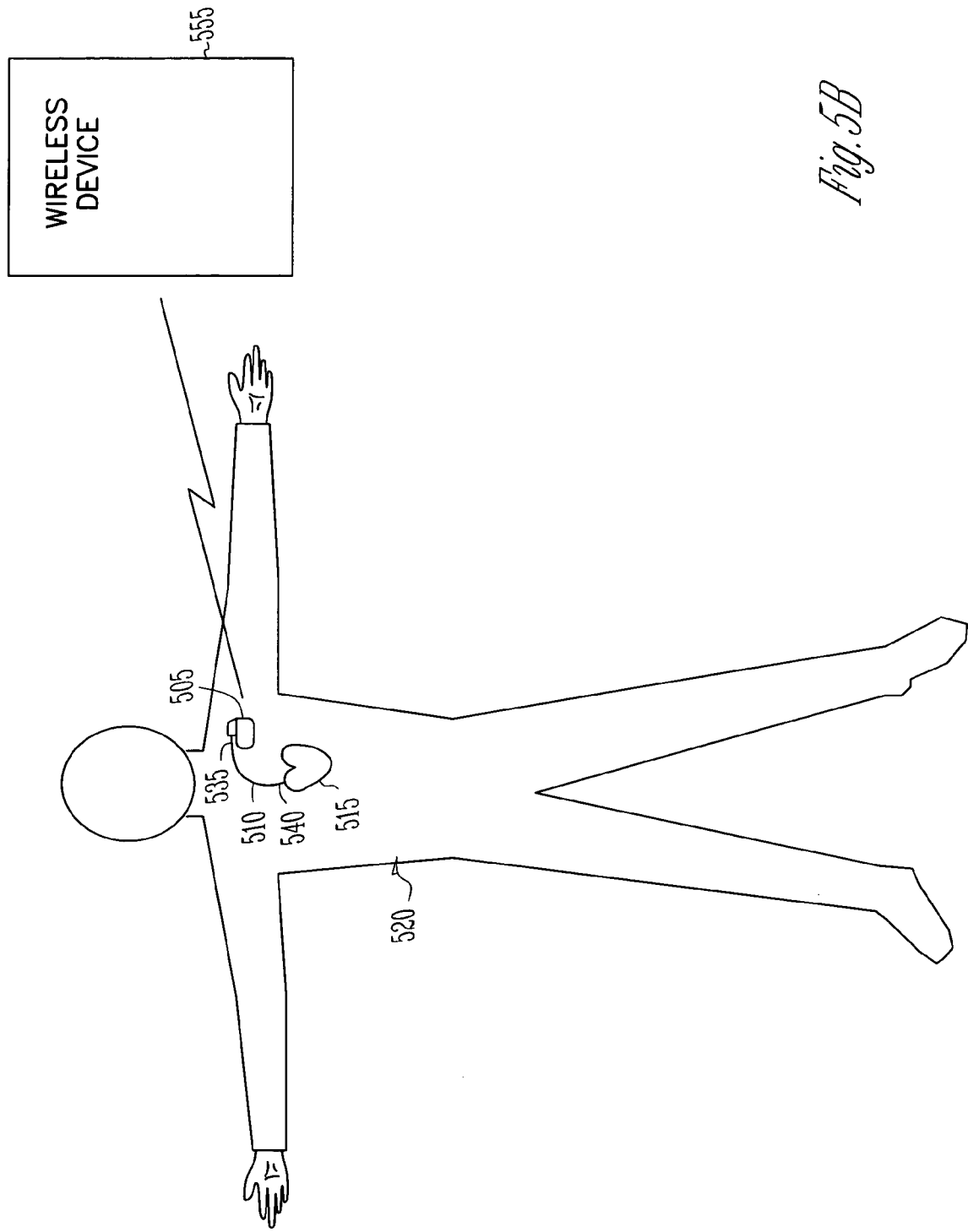

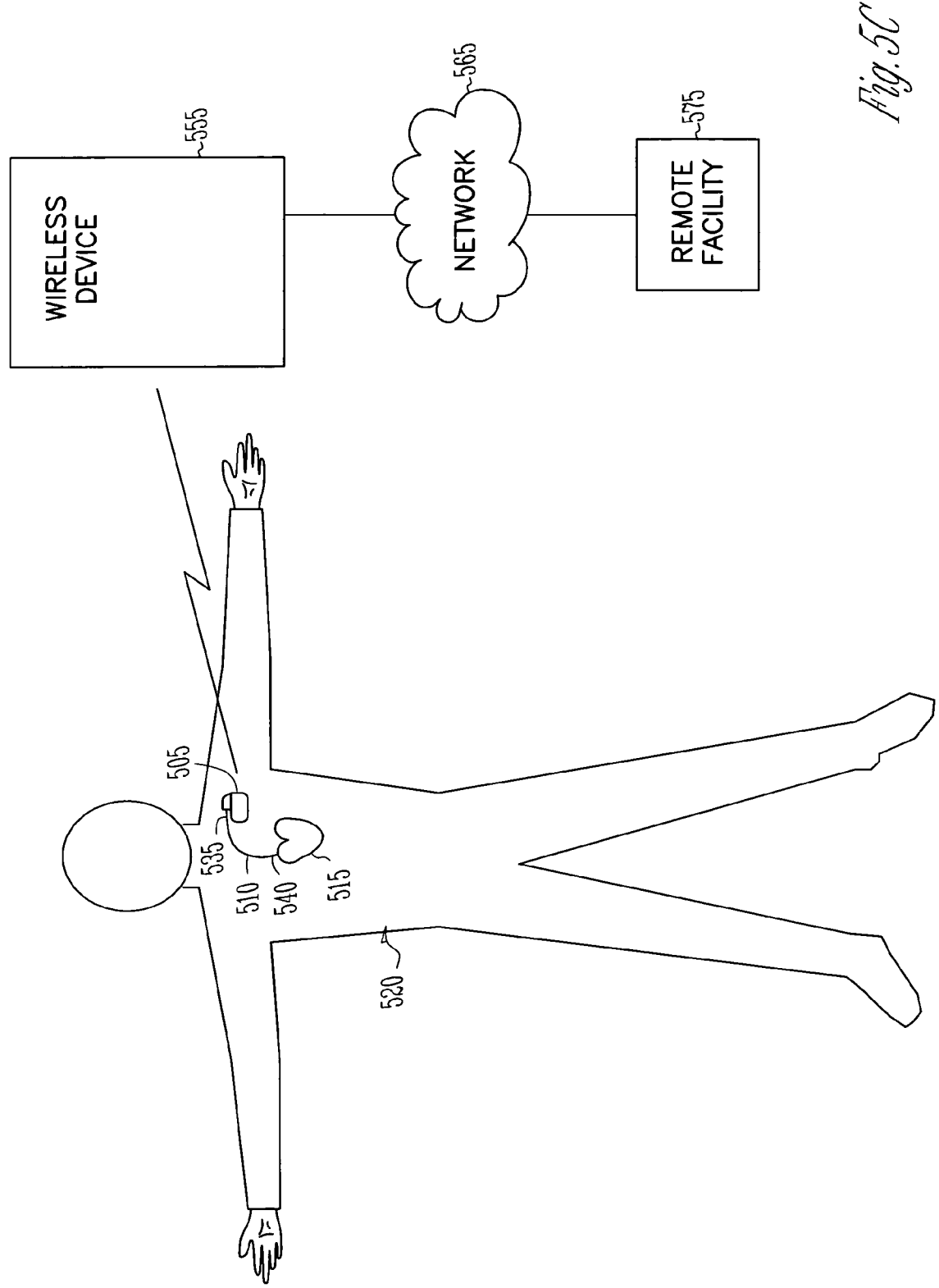

METHOD AND APPARATUS FOR CELL AND ELECTRICAL THERAPY OF LIVING TISSUE

CROSS-REFERENCE TO RELATED APPLICATION(S)

This application claims the benefit of U.S. Provisional Application No. 60/429,954, filed on Nov. 30, 2002, under 35 U.S.C. §119(e), which is hereby incorporated by reference.

This application is related to co-pending, commonly assigned U.S. patent application Ser. No. 10/722,115, "METHOD AND APPARATUS FOR CELL AND ELECTRICAL THERAPY OF LIVING TISSUE," filed on Nov. 25, 2003, which is hereby incorporated by reference.

TECHNICAL FIELD

This invention relates generally to combined cell and electrical therapy of living tissue and particularly, but not by way of limitation, to method and apparatus for conditioning living tissue using cell and electrical therapy with a cardiac rhythm management system.

BACKGROUND

The heart is a unique organ which pumps blood not only to the remaining portions of the body, but to itself. "Heart attacks" or myocardial infarctions occur when there is a loss of proper blood flow to the heart. When heart tissue does not get adequate oxygen, there is a high probability that heart muscle cells will die. The severity of a heart attack is measured by the amount and severity of heart damage.

Heart disease is a leading cause of death. Despite advances in the treatment of heart attacks, patients suffer decreased quality of life due to the damage caused by the heart attack. One such damage is chronic heart failure arising from the heart attack. The cardiac muscle cells, cardiomyocytes, which, in some circumstances, die during a heart attack either cannot be regenerated naturally by the heart or cannot be regenerated in sufficient quantities to repair the damage following a heart attack. Depending on the severity of damage to the heart muscle, cardiac output, heart value function, and blood pressure generating capacity can be greatly reduced. These results only exemplify some of the long-term devastating impacts of heart attacks on patients.

One way to treat damaged heart muscle cells is to provide pharmaceutical therapies in an effort to restore heart function. Such therapies may not be particularly effective if the damage to the heart is too severe, and pharmaceutical therapy is not believed to regenerate cardiomyocytes, but instead acts to block or promote certain molecular pathways that are thought to be associated with the progression of heart disease to heart failure.

Another treatment for damaged heart muscle cells is called "cell therapy." Cell therapy involves the administration of endogenous, autologous and/or or nonautologous cells to a patient. For example, myogenic cells can be injected into damaged cardiac tissue with the intent of replacing damaged heart muscle or improving the mechanical properties of the damaged region. However, the administration of myogenic cells does not ensure that the cells will engraft or survive, much less function and there is a need in the art for enhanced efficacy of cell therapies.

SUMMARY

This document discloses, among other things, a method and apparatus for synergistic actions among cell and electrical therapies of living tissue.

In varying embodiments, a system for electrical therapy of cardiac tissue of a heart, at least a portion of the cardiac tissue administered with exogenous cells in a cell therapy, including one or more catheter leads with electrodes; a pulse generator comprising an interface for connection to the one or more catheter leads, a controller programmable for a plurality of pulse delivery modes, and a sense amplifier for sensing electrical signals from the one or more catheter leads; and wherein the pulse generator includes a selectable pacing mode for providing therapeutic electrical stimulation to enhance the cell therapy of the cardiac tissue.

In various embodiments, the therapeutic electrical stimulation includes a VDD pacing mode having an atrioventricular delay which is short compared to an intrinsic atrioventricular delay of the heart.

Also described are embodiments where the therapeutic electrical stimulation is provided at times between additional pacing and defibrillation therapies, where the therapeutic electrical stimulation is programmable for certain times of day, such as for sleep times.

Also described are embodiments where the therapeutic electrical stimulation is programmable for certain levels of stress, or for certain levels of activity.

A variety of embodiments are provided where the therapy is invoked by a programmer, where accelerometer data is used to determine when to apply therapeutic electrical stimulation and where lead location is used to determine types of therapeutic electrical stimulation, for some examples.

Also discussed are methods for enhancing cell therapy of cardiac tissue including applying electrical therapy using an implantable pulse generator to cardiac tissue administered with exogenous cell therapy comprising donor cells, wherein the electrical therapy enhances one or more of engraftment, survival, proliferation, differentiation or function of the donor cells. Different methods including in vivo and in vitro treatments are discussed. Various pacing therapies are also discussed. In one embodiment, the methods include administering an agent that enhances exogenous cell engraftment, survival, proliferation, differentiation, or function. Enhancement of cardiac function and angiogenesis are also discussed.

The description also provides various catheters for cell therapy, including needle means for injection of fluids for cell therapy.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

In the drawings, like numerals describe similar components throughout the several views. Like numerals having different letter suffixes represent different instances of the components.

FIG. 5A is a diagram showing a programmer for use with an implanted cardiac rhythm management device according to one embodiment of the present invention.

FIG. 5B is a diagram showing a wireless device in communications with an implanted device for management of the implanted device and therapy according to one embodiment of the present invention.

FIG. 5C is a diagram showing a wireless device in communications with an implanted device and connected to a network for communications with a remote facility for management of the implanted device and therapy according to one embodiment of the present invention.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their equivalents.

It should be noted that references to "an", "one", or "various" embodiments in this disclosure are not necessarily to the same embodiment, and such references contemplate more than one embodiment.

General Overview

This document describes, among other things, method and apparatus for cell therapy and electrical conditioning of living tissue. In one embodiment, cell therapy is applied to tissue in vivo by locating damaged tissue and administering, e.g., inserting or applying, appropriate cellular material ("donor cells") into and/or to the damaged tissue. In one embodiment, the area including the damaged tissue and donor cells are then subjected to electric conditioning, such as pacing-level electrical stimulation, using a pulse generator with properly positioned electrodes. Several embodiments are presented below to provide examples of different therapy apparatus and method. It is understood that other apparatus and method are possible as provided by the attached claims and their equivalents.

Figure 1A:
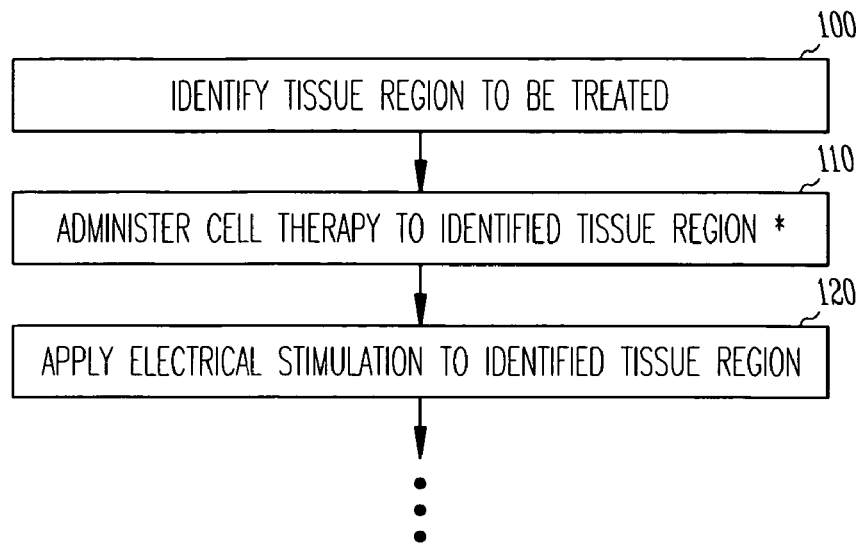
FIG. 1A is a flow diagram showing an overall therapy using cell therapy and electrical therapy according to one embodiment of the present invention.
Figure 1B:
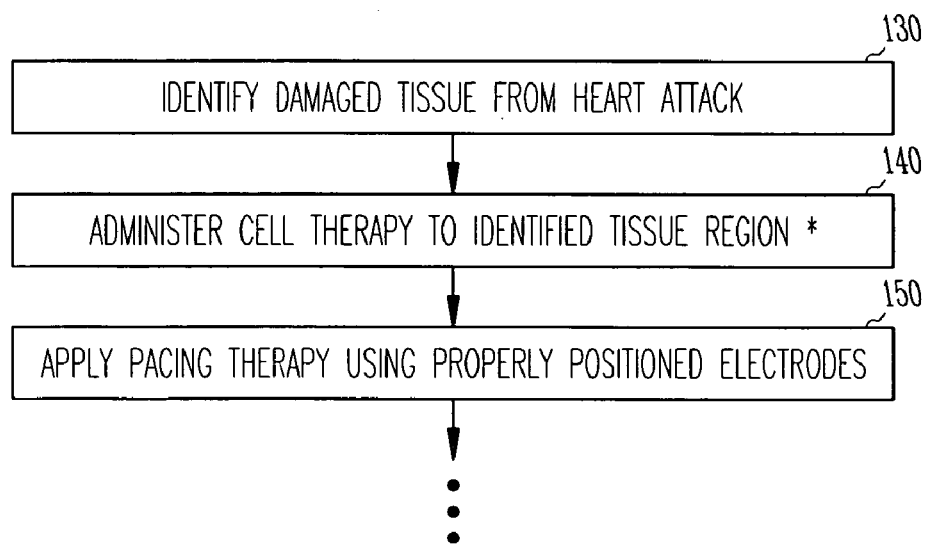
FIG. 1B is a flow diagram showing a particular therapy for treating cardiac tissue using combined cell and electrical therapies according to one embodiment of the present invention.

FIG. 1A shows a flow chart for providing combined cell and electrical therapy according to one embodiment of the present invention. A region of the tissue to be treated is identified 100. Cell therapy is administered to the identified region 110. Electrical therapy is applied to the identified region 120. In one approach, the cells ("donor" cells) are administered concurrently with electrical therapy, while in other approaches electrical therapy is subsequent to cell administration. In another approach electrical therapy is applied prior to cell administration. Moreover, it is understood that multiple cell therapies may be implemented prior to application of the electrical therapy to the identified tissue region. Also for example, the cell therapy may be followed by multiple electrical therapies. It is understood that different permutations of cell and electrical therapy may be performed in varying embodiments. For instance, electrical conditioning may be applied before, during, or after cell therapy. In one approach cellular engraftment, cellular proliferation, cellular differentiation, cellular survival and/or cellular function, e.g., contractile function, of the donor cells in the recipient is further enhanced by electrical stimulus from the electrical therapy.

In one embodiment an advanced patient management device is used to control the applied electrical therapy in conjunction with inputs regarding applied cell therapy, inputs regarding patient health, and inputs regarding environmental conditions. Other inputs are contemplated, and those provided herein are intended to demonstrate the flexibility and programmability afforded the user when the cell and electrical therapies are managed with an advanced patient management system. Such a system is discussed in various applications by the assignee, including, but not limited to, in U.S. patent application Ser. No. 10/093,353, filed Mar. 6, 2002, which is hereby incorporated by reference in its entirety.

Example of Cell Therapy of Cardiac Tissue

The present teachings are useful in a number of therapies. In one example, the treatment of a failing heart is possible. Such therapies may be employed for both ischemic and non-ischemic heart failure etiologies. In one example application where the damaged tissue to be treated is cardiac tissue, the cardiac tissue region (or regions) of damaged tissue are identified 130 and then cell therapy is administered to one or more areas of damaged tissue 140. Tissue damage resulting from a myocardial infarction or heart attack is one type of tissue treatable by these apparatus and methods.

Different methods of locating the damaged tissue may be employed. For example, electrophysiology, such as electrocardiograms, can be used to locate damaged cardiac tissue. Other locating methods include, but are not limited to: echocardiography and catheter-based voltage mapping of a portion of the heart; catheter based strain mapping; invasive or minimally invasive surgery (visualization of damaged tissue); and other imaging techniques, such as MRI, perfusion imaging, fluoroscopy, and angiography.

Once the damaged tissue is located, the localized area may be treated by inserting or applying donor cells, e.g., cells administered intravenously, transvenously, intramyocardially or by any other convenient route, and delivered by a needle, catheter, e.g., a catheter which includes an injection needle or infusion port, or other suitable device. Some exemplary delivery apparatus and methods include, but are not limited to, the teachings provided in the patent applications entitled: Drug Delivery Catheter with Retractable Needle, U.S. Ser. No. 09/746,498 filed Dec. 21, 2000; and Intra-Ventricular Substance Delivery Catheter System, U.S. Ser. No. 10/038,788, filed Dec. 31, 2001. Both of these disclosures are incorporated by reference in their entirety.

Figure 2A:
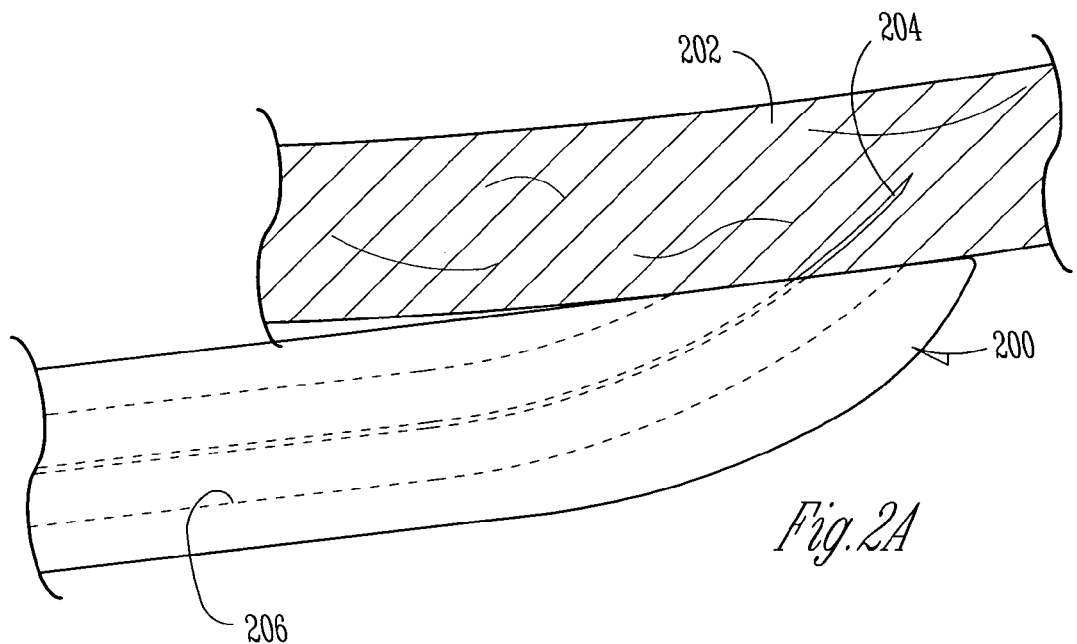
FIG. 2A is a drawing of a side view of a catheter tip for providing cell therapy according to one embodiment of the present invention.
Figure 2B:
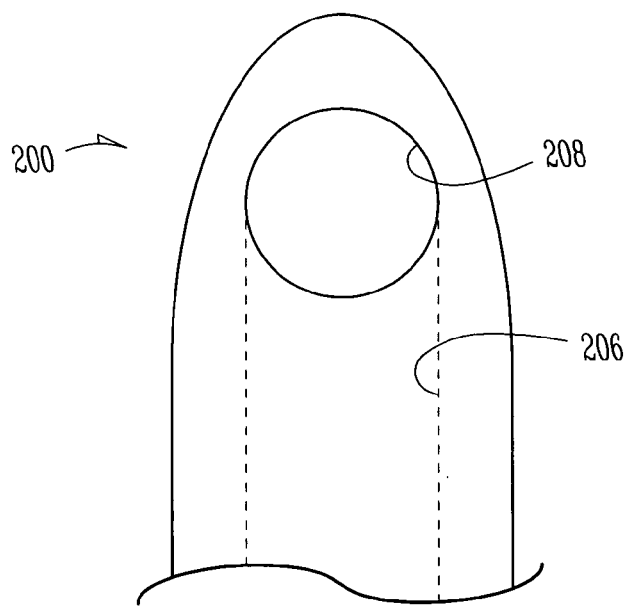
FIG. 2B is a drawing of a top view of a catheter tip for providing cell therapy according to one embodiment of the present invention.

In one embodiment, a catheter having a catheter tip 200 adapted for injection of exogenous cellular material is used for cell therapy. FIG. 2A shows a side view of a catheter tip 200 positioned near the myocardium 202 having damaged cardiac muscle tissue. The catheter tip 200 is positioned intrapericardially intravenously, transvenously, transarterially, intramyocardially, or by another method. A suction port 208 is shown from a top view in FIG. 2B at the distal end of the catheter. The catheter tip 200 is affixed near the region to be treated by a vacuum applied at the proximal end of the catheter to create a vacuum at the suction port 208 via channel 206 and thereby hold the catheter tip 200 against the myocardium 202. A hollow needle 204 is then advanced into the tissue at the catheter tip to inject exogenous cellular material to the location for cell therapy. After injection is complete, the hollow needle 204 is retracted into catheter tip 200 and the vacuum is removed so that the catheter tip 200 can be repositioned for therapy at a different location.

In one embodiment, the needle is deployed through a channel and and using an actuator at the proximal end of the catheter. In the example where a common channel is used between the vacuum and the needle, the vacuum channel is sealed where the needle exits the catheter at the proximal end to maintain any vacuum applied to the channel. The hollow needle in this embodiment uses a conduit from the proximal end to the distal end of the catheter. In one embodiment, injection of fluid is accomplished using a luer fitting and needle at the proximal end. Manipulation of the needle is accomplished using the actuator at the proximal end of the catheter.

The example demonstrated in FIG. 2A employs channel 206 for both the application of vacuum and a means for guiding hollow needle 204 and storing it when it is retracted. Other embodiments are provided herein where the suction port and needle use separate channels. For example, FIG. 2D shows a catheter tip 216 having suction port 218 with channel 220 and a hollow needle 222 with channel 224. In this example embodiment, channel 220 and channel 224 are separate. Other configurations are possible without departing from the scope of the present teachings.

In the embodiment with separate channels, a separate fitting for the vacuum and for the needle are used to apply the vacuum and inject fluid, respectively. In on embodiment a standard luer fitting is used and needle is used to inject the fluid.

Figure 2C:
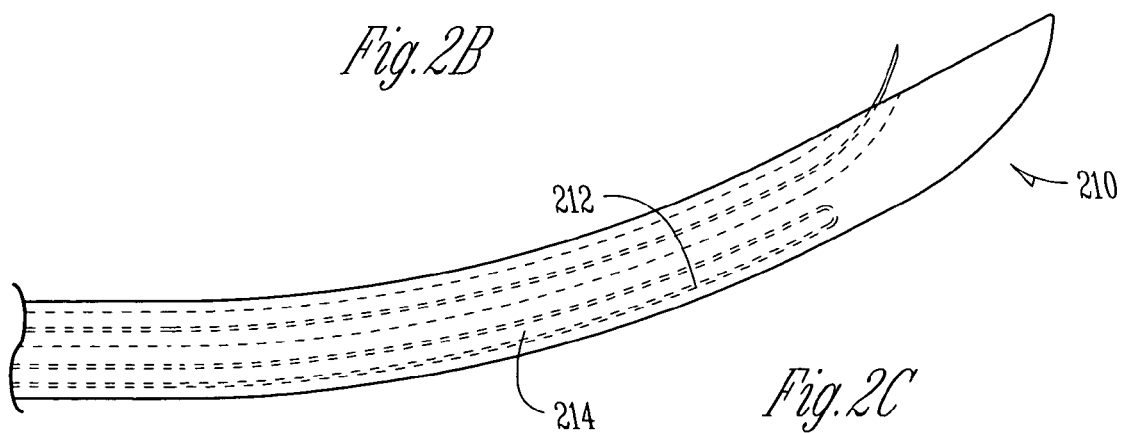
FIG. 2C is a side view of one embodiment of a catheter tip with adjustable curvature according to one embodiment of the present invention.
Figure 2D:
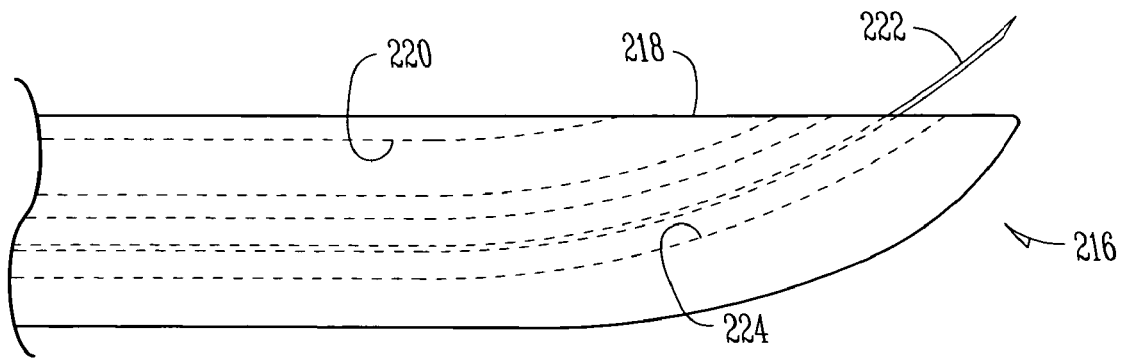
FIG. 2D is a drawing of a side view of a catheter tip with separate channels for vacuum and needle for providing cell therapy according to one embodiment of the present invention.

FIG. 2C shows one example of an embodiment where the catheter tip 210 is able to achieve an angle of curvature to provide a surface that conforms to a portion of a curved myocardium. In one embodiment, the angle of curvature is approximately 30 degrees. In varying embodiments the tip may be adjusted to perform differing degrees of deflection to adjustably position the suction port near the location to be treated. In one embodiment, the adjustment is performed using a stylet inserted into a pre-bent catheter tip portion. FIG. 2C demonstrates this by including a stylet channel 212 which accommodates stylet 214 in varying positions to show that as the stylet is removed, the angle of the tip changes and is thus adjustable. Other adjustment techniques may be employed without departing from the scope of the present teachings.

Figure 2E:
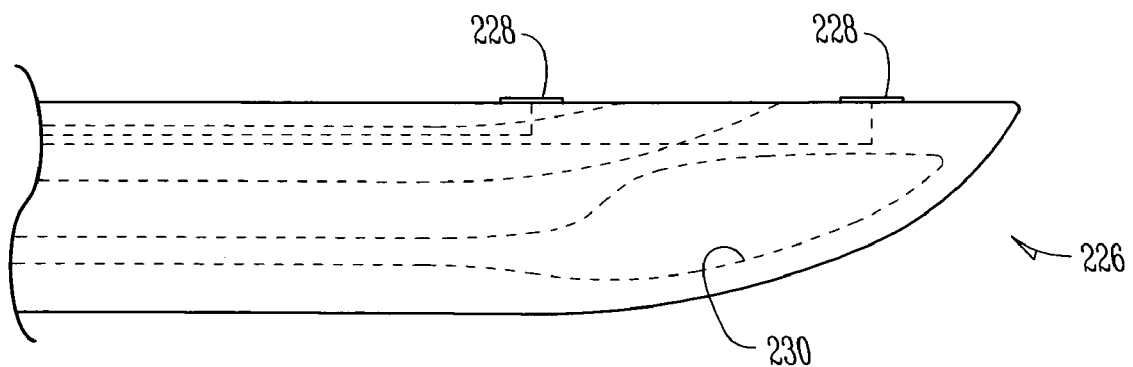
FIG. 2E is a drawing of a side view of a catheter tip with drug reservoir and electrodes for providing cell therapy according to one embodiment of the present invention.

FIG. 2E shows one embodiment of the catheter tip 226 where the tip is includes one or more contacts 228 connected to the proximal end and a drug reservoir 230 with elution means to perform iontophoresis. Various locations of possible electrode positions are demonstrated in FIG. 2E. In one embodiment, a chemical reservoir is included at the catheter tip for iontophoretic transfer into the adjacent tissue. In one embodiment, a porous electrode is used to transfer fluid from the catheter tip.

In varying embodiments, the catheter is dimensioned for different sizes to facilitate transvenous positioning of the cathode tip. In one embodiment, the catheter is available in diameters varying from 10 French to 24 French. Other sizes are possible without departing from the present teachings.

Figure 2F:
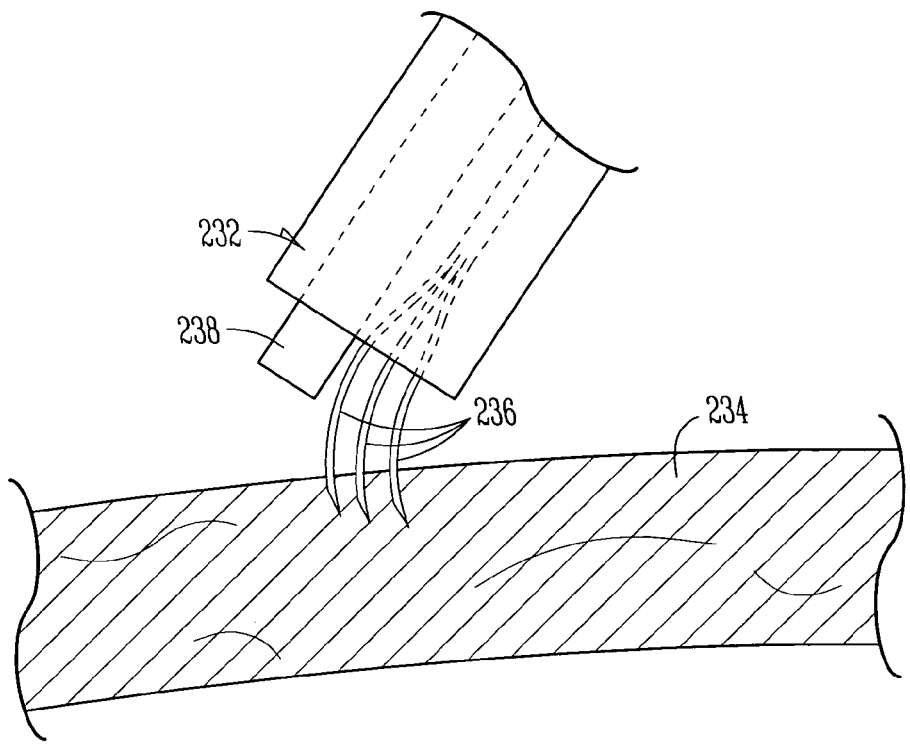
FIG. 2F is a drawing of a catheter tip having a needle array for providing cell therapy according to one embodiment of the present invention.

Another embodiment of a catheter tip for injection of exogenous cells is shown in FIG. 2F. In this example, the catheter tip 232 includes a needle array 236 which provides a plurality of needle points for injection into tissue 234. The needle array provides multiple pathways for delivery of material and lower delivery resistance. The catheter tip 232 also includes fiber optic 238 for visualizing the region and locating the catheter tip 232 for treating tissue 234.

In one embodiment, the needle array 236 is retractable for ease of transvenous and transarterial delivery. In one embodiment, the needle array 236 includes needle points that are approximately 0.5 cm in length. In varying embodiments, the needle array includes needles of varying lengths to provide a contour of tip points. In varying embodiments the needle array provides 2-3 mm of penetration into tissue. Other embodiments are possible without departing from the scope of the present teachings.

Figure 2G:
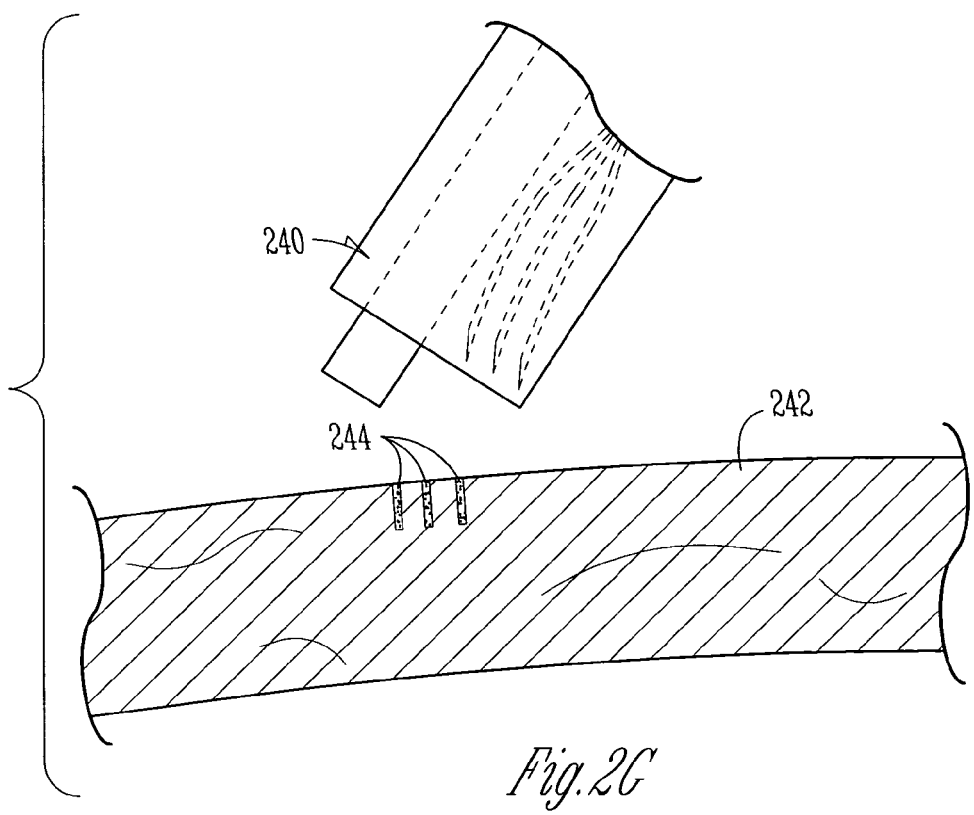
FIG. 2G is a drawing of the catheter tip of FIG. 2F with the needle array retracted and tissue after cell therapy according to one application of the present invention.

In one application demonstrated by FIG. 2G, a plurality of columns 244 of material are injected into tissue 242 by catheter tip 240. (The catheter tip 240 is shown in a retracted mode in FIG. 2G.) The columns 244 may contain cellular material and/or drugs and serve as passive molecule factories in tissue 242.

It is understood that the number and placement of tines may vary. Diameters and distances provided herein are intended to provide nonexclusive examples and are not intended in an exclusive or limiting sense.

Figure 2H:
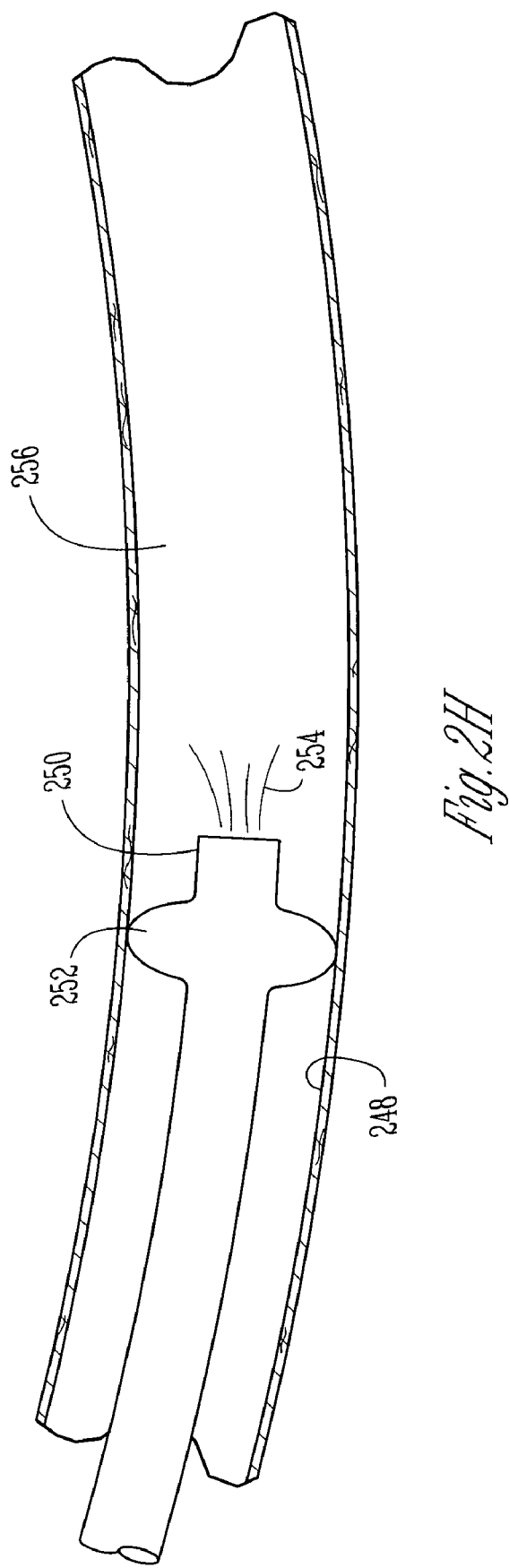
FIG. 2H is a drawing of a catheter tip with expandable balloon for cell therapy according to one embodiment of the present invention.

Another embodiment of a catheter-based delivery system includes the use of a balloon and delivery catheter. FIG. 2H shows one example of a catheter tip 250 which is insertable transvenously and transarterially for the delivery of cellular materials to a vessel or organ. Catheter tip 250 includes balloon 252 for occluding the lumen 248 and providing a temporary blockage for the material 254 to remain in space 256 for a period of time. Space 256 is treated with the cellular material, and then balloon 252 is deflated for withdrawal of the catheter tip 250.

It is understood that various combinations of the examples provided above are possible. For example, a fiber optic may be used to place the catheter tip and may be combined with the catheter tips having common and independent channels for the vacuum and the needle and or needle array. Other combinations are possible without departing from the scope of the present teachings.

Combined cell and electrical therapy may also be accompanied by the administration of drugs to the recipient animal.

Variations in design and placement of elements may be implemented without departing from the teachings provided herein, and the examples given are not intended in a limited or exclusive sense.

Sources of Donor Cells for Cell-Based Therapies

Sources for donor cells in cell-based therapies include skeletal muscle derived cells, for instance, skeletal muscle cells and skeletal myoblasts; cardiac derived cells, myocytes, e.g., ventricular myocytes, atrial myocytes, SA nodal myocytes, AV nodal myocytes, and Purkinje cells; bone marrow-derived cells, e.g., mesenchymal cells and stromal cells; smooth muscle cells; fibroblasts; or pluripotent cells or totipotent cells, e.g., teratoma cells, hematopoietic stem cells, for instance, cells from cord blood and isolated $CD34^+$ cells, multipotent adult progenitor cells, adult stem cells and embryonic stem cells. In one embodiment, the donor cells are autologous cells including xenologous cells, however, non-autologous cells may be employed. The donor cells can be expanded in vitro to provide an expanded population of donor cells for administration to a recipient animal. In addition, donor cells may be treated in vitro to cause a preferred differentiation. Sources of donor cells and methods of culturing those cells are known to the art. See, for example, U.S. Pat. No. 5,130,141 and Jain et al. (*Circulation*, 103, 1920 (2001)), wherein the isolation and expansion of myoblasts from skeletal leg muscle is discussed (see also Suzuki et al., *Circulation*, 104, I-207 (2001), Douz et al., *Circulation*, III-210 (2000) and Zimmerman et al., *Circulation Res.*, 90, 223 (2002)). Published U.S. application 20020110910 discusses the isolation of and media for long term survival of cardiomyocytes. U.S. Pat. No. 5,580,779 discusses isolating myocardial cells from human atria and ventricles and inducing the proliferation of those myocardial cells. U.S. Pat. No. 5,103,821 discusses isolating and culturing SA node cells. For SA node cells, the cells may be co-cultured with stem cells or other undifferentiated cells. U.S. Pat. No. 5,543,318 discusses isolating and culturing human atrial myocytes. U.S. Pat. Nos. 6,090,622 and 6,245,566 discusses preparation of embryonic stem cells, while U.S. Pat. No. 5,486,359 discusses preparation of mesenchymal cells.

The donor cells may also be manipulated in vitro to introduce one or more desirable gene products (transgenes) to the cells. Preferably, the transgenic donor cells include a transgene that enhances cellular proliferation, cellular engraftment, cellular survival, cellular differentiation and/or cellular function of the donor cells in the recipient. The expression of one or more transgenes may be employed to decrease, replace or supplement (increase) the expression of endogenous genes in the donor cells, e.g., if the donor cells are autologous cells and the donor has an inherited or acquired disease associated with aberrant expression of an endogenous gene in cardiac cells. The expression of one or more transgenes may correct the level of the gene product encoded by the transgene in the donor cells. In one embodiment the expression of the transgene is controlled by a regulatable or tissue-specific, e.g., cardiac myocyte-specific promoter. The transgene may be introduced to donor cells by any means including but not limited to liposomes, electroporation, naked DNA, or viral-mediated transduction, for instance, via adenovirus, adeno-associated virus, retrovirus or lentivirus vectors.

Compositions, Dosages and Routes of Administration of the Donor Cells

Compositions of the invention comprise donor cells, including cells from different sources, and optionally agents that enhance donor cell engraftment, survival, proliferation and/or differentiation, enhance cardiac function or stimulate angiogenesis. The cells to be administered may be a population of individual cells or cells grown in culture so as to form a two dimensional or three dimensional structure. The number of cells to be administered will be an amount which results in a beneficial effect to the recipient. For example, from $10^2$ to $10^1$, e.g., from $10^3$ to $10^9$, $10^4$ to $10^8$, or $10^5$ to $10^7$, cells can be administered to, e.g., injected, the region of interest, for instance, infarcted and tissue surrounding infarcted tissue. Agents which may enhance cardiac function or stimulate angiogenesis include but are not limited to pyruvate, catecholamine stimulating agents, fibroblast growth factor, e.g., basic fibroblast growth factor, acidic fibroblast growth factor, fibroblast growth factor-4 and fibroblast growth factor-5, epidermal growth factor, platelet-derived growth factor, vascular endothelial growth factor (e.g., $VEGF_{121}$, $VEGF_{145}$, $VEGF_{165}$, $VEGF_{189}$ or $VEGF_{206}$), tissue growth factors and the like. Such agents may optionally be present in the compositions of the invention or administered separately.

The cells are administered during a prophylactic, diagnostic or therapeutic vascular procedure or an invasive or minimally invasive surgical procedure. In one embodiment, the cells are administered post-MI, within hours, e.g., 1 to 12 hours, to days, e.g., 1 to 2 days, and up to one or more weeks after MI. Preferably, the administration of donor cells is prior to scar formation. The cells may be administered intravenously, transvenously, intramyocardially or by any other convenient route, and delivered by a needle, catheter, e.g., a catheter which includes an injection needle or infusion port, or other suitable device. Some exemplary delivery apparatus and methods include, but are not limited to, the teachings provided herein.

In one embodiment, once administered, the donor cells develop functional connections with adjacent cells, membrane channels with adjacent cells, including viable cells in the recipient, and, if not already differentiated, differentiate to myocardial cells.

Example of Electrical Therapy of Cardiac Tissue

Following cell therapy, the identified region of tissue to be treated is subjected to electrical therapy 150. In the example of cardiac tissue, electric current is imposed across or adjacent to the damaged tissue. In one embodiment a pacemaker with implanted catheter leads is employed to provide the appropriate pacing stimulation to the identified region of tissue. In varying embodiments, one or more electrodes serve to apply an electric field over portions of the identified tissue region. In implanted pacemaker applications the pacemaker housing may serve as an electrode.

In one embodiment, the pacemaker is programmed to perform VDD pacing using an atrioventricular delay which is relatively short when compared to the intrinsic atrioventricular interval. In such embodiments, the electrical pace wavefront is near the infarcted region very early in the cardiac cycle so as to electrophysiologically capture and mechanically unload the identified region with the pacing stimulus. The VDD mode of the pacemaker allows the heart to maintain a rate near to that of a normal sinus rhythm, providing better control of the activation pattern; the ventricles are pre-excited without advancing the pacing rate unnecessarily. In this way, the depolarization wavefront fuses with the paced complex, resulting in the most intrinsic activation of the ventricles, yet providing for the pre-excitement of the damaged tissue region. Other pacing modes are possible, and those provided here are not intended in an exhaustive or exclusive sense.

In varying embodiments and combinations, the electrical therapy includes different programming modes for use with a particular cell therapy. In one embodiment, electrical therapy is invoked during periods of relative inactivity such as are common during nocturnal sleep to condition the cardiac tissue and improve cell engraftment. In one embodiment, electrical therapy is invoked based on physical activity of the patient during which heart wall stress is reduced via electrical pre-excitation. Such physical activity may be measured by detection of accelerometer data. In one embodiment, the electrical therapy is invoked for certain times of day or during specifically programmed, recurring patterns of intrinsic (M beats) and paced beats (N beats) in a ratio of M:N. In embodiments featuring programmable microprocessors, the time of day is downloaded to the microprocessor upon programming and therapy is programmably selectable. In varying embodiments and combinations, electrical therapy is delivered upon preselected sensor inputs. For example, electrical therapy is invoked (continuous or M:N patterns) upon detected patient activity. In one embodiment, electrical therapy is invoked upon detection of patient stress. In one embodiment, electrical therapy is invoked upon detection of patient metabolic high stress in the heart, such as in sleep, where ventricles are distended and filling better. In one embodiment internal pressure is measured to determine local stress. Different sensors may be employed to determine conditions for delivery of electrical therapy.

Additional programming modes are contemplated by the present description. For example, in one embodiment a variable programming mode incorporates traditional electrical pacing interspersed with specialized cell therapy pacing cycles. In one embodiment, such pacing is used to provide complementary pacing therapies to a patient's heart to provide multiple benefits. In one embodiment, the varying pacing is applied using a duty-cycle approach. For example, a ratio of pacing of a first type to a pacing of a second type is programmed into the implantable device to provide a plurality of pacing therapies to a patient. This provides a new pacing mode where the programmability of duty cycle affords electrical therapy that complements at least one other pacing therapy and the administered cell therapy.

Another pacing variation provides a dynamically changing atrioventricular delay. In one exemplary embodiment, an atrioventricular delay is increased over a predetermined time period. For one example, an atrioventricular delay is lengthened by approximately one (1) millisecond each day over a predetermined time, such as three (3) months. In one embodiment, the atrioventricular delay is lengthened by 10 milliseconds over a predetermined amount of time, such as 2 months. In such embodiments, incremental increase in atrioventricular delay results in progressively loading a cardiac region, based on location of the electrodes. Similar but opposite effects might be obtained by progressively shortening the atrioventricular delay. Certain areas of the myocardium might be progressively unloaded, resulting in desired phenotypical changes at the chamber, tissue and cell levels.

Other embodiments and combinations are possible without departing from the scope of the present therapy system. The foregoing examples are intended to demonstrate some varying embodiments of the present therapy system, and are not intended in an exclusive or exhaustive sense.

In one embodiment, the pacing lead is positioned as close as possible to the site of engraftment. Positioning is performed using electrophysiology (e.g., ECG), echocardiographic mapping, or catheter based voltage mapping of the heart. Other location methods are possible without departing from the scope of the present teachings.

Lead placement is possible using epicardial leads implanted with minimal thorocotomy, and/or catheter leads. Treatment of the left ventricular region is possible using leads positioned in the coronary venous structures.

It is understood that a plurality of infarcted tissue regions may be treated using multiple cell and electrical therapy treatments.

Non-human animal models, e.g., rodent, lapine, canine or swine models, may be employed to determine pacing and cellular parameters useful to inhibit or treat a particular indication or condition. See, e.g., Jain et al., supra; Suzuki et al., supra; Pouleur et al., *Eur. J. Clin. Investig.*, 13, 331 (1983); Hammond, *J. Clin. Res.*, 92, 2644 (1993); Taylor et al., *Proc. Assoc. Am. Phys.*, 109, 245 (1997); and Roth et al., *J. Clin. Res.*, 91, 939 (1993)). For an animal model of MI, efficacious pacing and cell therapy results in improvement in cardiac function, e.g., increased maximum exercise capacity, contractile performance, and propagation velocity, decreased deleterious remodeling, decreased post-scar expansion, decreased apoptosis, increased angiogenesis, and increased donor cell engraftment, survival, proliferation, and function. Donor cell function can be determined using biochemical markers, e.g., myotube formation in grafted donor cells, the presence and/or levels of $\alpha$-actinin, titin, myomesin, sarcomeric myosin heavy chain, $\alpha$-actin and the like, and gap junction proteins (see Pimentel et al., *Circulation Res*, 90, 671 (2002)), as well as by improvements in global and regional cardiac function in recipients of donor cells. In ex vivo models, systolic and diastolic pressure-volume relations can be used to determine the efficacy of a particular therapy.

Example Cardiac Function Management Device

Figure 3:
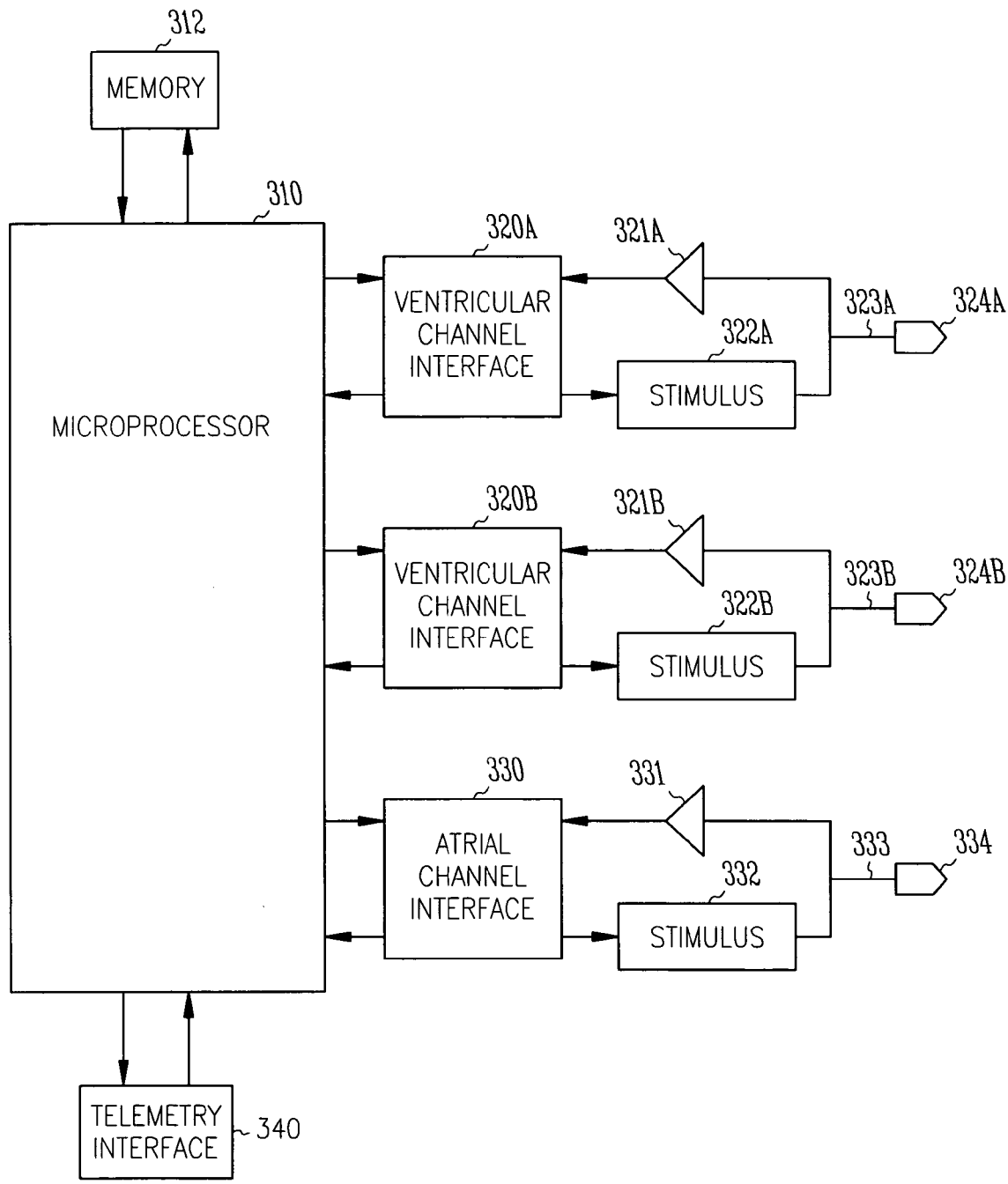
FIG. 3 is a block diagram of a pacemaker according to one embodiment of the present invention.

FIG. 3 shows a pacemaker performing the electrical therapy described herein. As used herein, the term pacemaker should be taken to mean any cardiac rhythm management device for pacing the heart and includes implantable pacemakers, external pacemakers, and implantable cardiac defibrillator/converters having a pacing functionality. A block diagram of a cardiac pacemaker having two ventricular pacing channels is shown in FIG. 3. Microprocessor 310 communicates with a memory 312 via a bidirectional data bus. In varying embodiments memory 312 comprises a ROM or RAM for program storage and a RAM for data storage. In one embodiment, the control unit includes dedicated circuitry either instead of, or in addition to, the programmed microprocessor for controlling the operation of the device. In one embodiment, the pacemaker employs a programmable microprocessor to implement the logic and timing functions for operating the pacemaker in accordance with a specified pacing mode and pacing parameters as well as for performing the data acquisition functions. A telemetry interface 340 is also provided for communicating with an external programmer. Such an external programmer may be used to change the pacing mode, adjust operating parameters, receive data stored by the device, and issue commands that affect the operation of the pacemaker. Such an interface also provides communications with advanced patient management devices, such as portable computers, PDA's, and other wireless devices as described herein and provided by the documents incorporated herein.

In embodiments incorporating physical motion detection for application of therapy the pacemaker includes sensors to detect exercise. For example, accelerometers and minute ventilation sensors may be incorporated for these purposes. Some embodiments may incorporate time of day for application of therapy. Such embodiments may include timing modules and may update them using information from a programmer or other wireless device.

The pacemaker has atrial sensing/stimulation channels comprising electrode 334, lead 333, sensing amplifier/filter 331, pulse generator 332, and an atrial channel interface 330 which communicates bidirectionally with a port of microprocessor 310. The device also has two ventricular sensing/stimulation channels that include electrodes 324A-B, leads 323A-B, sensing amplifiers 321A-B, pulse generators 322A-B, and ventricular channel interfaces 320A-B where "A" designates one ventricular channel and "B" designates the other. For each channel, the same lead and electrode are used for both sensing (i.e., detecting P-waves and R-waves) and stimulation. The ventricular electrodes could be disposed in each of the ventricles for biventricular pacing or in only one ventricle for multi-site pacing of that ventricle. The channel interfaces 320A-B and 330 include analog-to-digital converters for digitizing sensing signal inputs from the sensing amplifiers and registers which can be written to by the microprocessor in order to output stimulation pulses, change the stimulation pulse amplitude, and adjust the gain and threshold values for the sensing amplifiers. After digitization of the sensed signals by the channel interfaces, the signal samples can be processed in the digital domain by algorithms executed by the microprocessor in order perform further filtering. The detection of R wave and P wave peaks for timing purposes can also be performed digitally. Alternatively, a standard peak detection circuit could be used.

In one embodiment, the lead system includes endocardial leads, although other types of leads, such as epicardial leads, could also be used within the scope of the present teachings. In one embodiment, a first ventricular lead system is adapted for placement in a first cardiac region of the heart. In one example, the first cardiac region of the heart is within the coronary sinus and/or the great cardiac vein of the heart adjacent to the left ventricle. In one embodiment, the first lead system includes a number of electrodes and electrical contacts. A tip electrode is located at, or near, the distal end of the first lead system, and connects electrically to terminal through a conductor provided within the first lead system. The first lead system also includes a proximal electrode which is spaced proximal the tip electrode. In one embodiment, the proximal electrode is spaced proximal the tip electrode for placement adjacent to the left ventricle of the heart. The proximal electrode is electrically connected to terminal through an internal conductor within the first lead system. The proximal electrode can be of either an annular or a semi-annular construction, encircling or semi-encircling the peripheral surface of the first lead system.

The pacemaker further includes a second ventricular lead system. In one embodiment, the second lead system is an endocardial lead, although other types of leads, such as epicardial leads, could be used within the scope of the present teachings. The second ventricular lead system is adapted for placement within a second cardiac region of the heart. In one example, the second cardiac region of the heart is the right ventricle of the heart. In one embodiment, the second lead system includes a number of electrodes and electrical contacts. For example, in one embodiment, a tip electrode is located at, or near, the distal end of the second lead system, and connects electrically through a conductor provided in the lead, for connection to terminal. The second lead system further optionally includes a first defibrillation coil electrode spaced proximal to the distal end for placement in the right ventricle. The first defibrillation coil electrode is electrically connected to both terminals and through internal conductors within the body of the second lead system. The second lead system also optionally includes a second defibrillation coil electrode, which is spaced apart and proximal from the distal end of the second lead system such that the second defibrillation coil electrode is positioned within the right atrium or major vein leading to the right atrium of the heart. The second defibrillation coil electrode is electrically connected to terminal through an internal conductor within the body of the second lead system.

In varying embodiments, the system includes multiple atrial electrodes and optionally includes the defibrillation components. The configuration and placement of electrodes may vary without departing from the scope of the present teachings.

In one embodiment, the pacemaker is a programmable microprocessor-based system, with a microprocessor and memory, which contains parameters for various pacing and sensing modes. Pacing modes include, but are not limited to, normal pacing, overdrive or burst pacing, and pacing for prevention of ventricular tachyarrhythmias. The system also includes means for adjusting atrioventricular delay. The microprocessor further includes means for communicating with an internal controller, in the form of an RF receiver/transmitter. This includes an antenna, whereby it may receive and transmit signals to and from an external controller. In this manner, programming commands or instructions can be transferred to the microprocessor after implant. In one embodiment operating data is stored in memory during operation. This data may be transferred to the external controller for medical analysis.

In one embodiment, pacing pulses are controlled by the microprocessor to carry out a coordinated pacing scheme at the two ventricular pacing locations. Pacing modes include, but are not limited to, normal sinus rhythm pacing modes, overdrive or burst pacing modes for treating ventricular tachyarrhythmia, and/or pacing regimens for preventing the onset of a ventricular tachyarrhythmia. Additional advantages for providing pacing from the two ventricular pacing locations include the ability for either one of the two pacing systems to serve as a back-up pacing system and location for the other in the event that one pacing system were to fail.

Atrial sensing circuit is coupled by an atrial lead to a heart for receiving, sensing, and/or detecting electrical atrial heart signals. Such atrial heart signals include atrial activations (also referred to as atrial depolarizations or P-waves), which correspond to atrial contractions. Such atrial heart signals include normal atrial rhythms, and abnormal atrial rhythms including atrial tachyarrhythmias, such as atrial fibrillation, and other atrial activity. An atrial sensing circuit provides one or more signals to controller to indicate, among other things, the presence of sensed intrinsic atrial heart contractions.

An atrial therapy circuit provides atrial pacing therapy, as appropriate, to electrodes located at or near one of the atria of the heart for obtaining resulting evoked atrial depolarizations. In one embodiment, the atrial therapy circuit also provides cardioversion/defibrillation therapy, as appropriate, to electrodes located at or near one of the atria of the heart, for terminating atrial fibrillation and/or other atrial tachyarrhythmias.

Although FIG. 3 shows a human with an implanted cardiac rhythm management device, it is understood that the teachings may be used with devices other than cardiac rhythm management devices. The teachings are also applicable to non-mammalian heart therapies. Those skilled in the art, upon reading and understanding the present description, shall appreciate other uses and variations within the scope of the present teachings.

Figure 4:
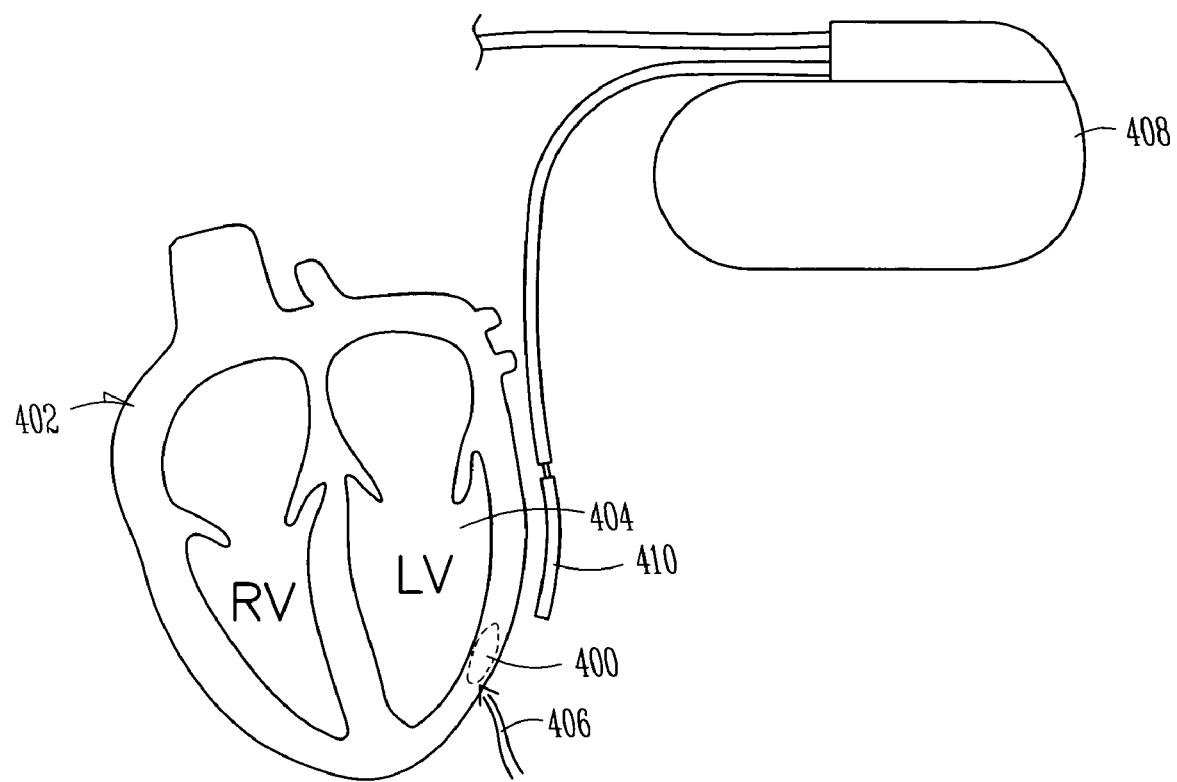
FIG. 4 shows one example of application of cell and electrical therapy to a region of cardiac tissue subject to myocardial infarction according to one embodiment of the present invention.

FIG. 4 shows one example of administration of cell therapy and electrical therapy to a region of cardiac tissue subject to myocardial infarction. The heart 402 includes a left ventricle 404 which has tissue injured by a myocardial infarction 400. The affected region 400 is determined by methods including those described herein. Cell therapy 406 is preferably administered in close proximity to, e.g., transvenously, transarterially, intramyocardially or in adjacent non-infarcted tissue, and/or directly to the affected region 400 and electrical therapy is applied using a programmable pulse generator 408 and lead 410.

The electrical therapy includes pacing in vivo preferably near infracted or hybernating myocardium and including sites targeted for cell therapy to enhance the engraftment, survival, proliferation, and/or function, and optionally the differentiation, of the cells. The pacing may be applied to lessen local stress and strain that might otherwise inhibit the successful engraftment of donor cells including the successful formation of gap junctions between donor cells and noninfarcted recipient myocardial cells. Such therapy thus affects both mechanical and electrical connections to neighboring cells of the native myocardium. In particular, pacing at or near such sites may enhance development of new gap junctions which may be needed for coordinating the function of the donor cells with that of the native myocardium. The therapy also operates to control metabolic demands at the site of targeted cell therapy to increase donor cell viability. Another benefit is that electrical stimulation of myocytes promotes release of factors that encourage angiogenesis. In one embodiment, preconditioning of cells cultured in vitro, e.g., with drugs or other chemical agents, and/or transgene expression, and/or electrical stimulation and/or mechanical stimulation, may benefit in vivo engraftment, survival, proliferation, differentiation and/or functioning of the cells.

In vivo left ventricle pacing controls local stress by managing atrioventricular delay, RV-LV offset, stimulation site alternation, heart rate, and pacing waveform parameters. The LV stimulus also promotes donor cell engraftment, survival, proliferation, differentiation and/or functioning in vivo and is controllable based on pacing waveform, rate, and site.

In one embodiment, the pacemaker is programmed to perform VDD pacing using an atrioventricular delay which is relatively short when compared to the intrinsic atrioventricular interval. Other electrical therapies are possible given the teachings herein. For example, it is possible that the affected region is pre-treated to strengthen the region before injection of cell therapy. Upon reading and understanding the teachings provided herein, those skilled in the art will understand other electrical therapies are possible without departing from the scope of the present teachings.

FIG. 5A is a schematic drawing illustrating, by way of example, but not by way of limitation, one embodiment of portions of a cardiac rhythm management system 500 and an environment in which it is used. System 500 includes an implantable cardiac rhythm management device 505, also referred to as an electronics unit, which is coupled by an intravascular endocardial lead 510, or other lead, to a heart 515 of patient 520. System 500 also includes an external programmer 525 providing wireless communication with device 505 using a telemetry device 530. Catheter lead 510 includes a proximal end 535, which is coupled to device 505, and a distal end 540, which is coupled to one or more portions of heart 515. Although FIG. 5A shows a human with an implanted cardiac rhythm management device, it is understood that the teachings may be used with devices other than cardiac rhythm management devices. The teachings are also applicable to non-mammalian heart therapies. Those skilled in the art, upon reading and understanding the present description, shall appreciate other uses and variations within the scope of the present teachings.

FIG. 5B is a diagram showing a wireless device in communications with an implanted device for management of the implanted device and therapy according to one embodiment of the present invention. In one embodiment, wireless device 555 is used to conduct communications with pacemaker 505. In one application, wireless device 555 is a personal digital assistant (PDA). In one embodiment, wireless device 555 is a computer with wireless interface. In one embodiment, wireless device 555 is a cellular phone. The communications between pacemaker 505 and wireless device 555 can be used for coordinating operations and therapies of the pacemaker and/or to communicate device operations and physiological data to another site in communications with the wireless device 555. FIG. 5C shows one example of communications where a network 565 is in contact with wireless device 555. The connection between wireless device 555 and network 565 can be either wired or wireless. In one embodiment, network 565 is the Internet. Remote facility 575 is a medical facility or location which a doctor or health care provider can access data from the pacemaker 505. Alternatively, data and/or instructions can be transmitted from the remote facility 575 to the wireless device 555 and/or the pacemaker 505. Alternatively, instructions and data can be transferred bidirectionally between the remote facility, wireless device, and/or pacemaker 505.

The network is a communication system that interconnects a number of computer processing units when those units are some distance away from one another, but within the same contiguous property to allow private communications facilities to be installed. The network may also include the facility to allow multiple compute processors to communicate with each other when some or all of those processors are within the same enclosure and connected by a common back plane.

Connections with a remote facility and wireless device are useful for advanced patient management. Some exemplary apparatus and methods for patient management include, but are not limited to, the teachings provided in the patent application entitled: Method and Apparatus for Establishing Context Among Events and Optimizing Implanted Medical Device Performance, U.S. Ser. No. 10/093,353 filed Mar. 6, 2002, which is incorporated by reference in its entirety.

Combined Cell and Electrical Therapy Example

In one embodiment, skeletal muscle cells are obtained from a patient who recently, e.g., within the previous 1 to 7 days, suffered a myocardial infarction. The skeletal muscle cells may be cultured in vitro, e.g., so as to expand the population, or may be employed in the absence of culturing. Prior to cell therapy, the damaged tissue in the patient is located by conventional means, e.g., an electrocardiogram. The autologous donor skeletal muscle cells, prior to administration to the damaged tissue, may be optionally subjected to washing to remove non-cellular components, i.e., components which are not intact cells including components in tissue culture media, and introduced to the damaged tissue in a physiologically compatible carrier (vehicle), e.g., an aqueous, semi-solid or solid vehicle. In one embodiment, approximately $10^2$ to $10^{10}$ donor skeletal muscle cells are administered via a catheter, which includes an injection needle, plurality of needles, or infusion port, positioned at or near the damaged tissue. A biocompatible (e.g., biodegradable) marker may be administered with the skeletal muscle cells so as to monitor the site(s) of administration of the donor cells and, optionally, later identify the treated region. Once administered, the donor cells develop functional connections with adjacent viable cells, and membrane channels with adjacent viable cells.

In one embodiment, the area including the damaged tissue and donor cells in the patient are then subjected to electric conditioning, such as pacing-level electrical stimulation, using a pulse generator with properly positioned electrodes, which in combination with cell therapy results in an improvement in global and regional cardiac function in the patient. A pacing regimen is provided where the pacemaker is programmed to perform VDD pacing using an atrioventricular delay which is relatively short when compared to the intrinsic atrioventricular interval.

In General

Although the present therapy is described in the example of cardiac therapy, it is understood that many other applications are possible. Such teachings may be applied to in vitro and in vivo treatment of other organs and blood vessel growth.

It is to be understood that the above description is intended to be illustrative, and not restrictive. Other embodiments will be apparent to those of skill in the art upon reviewing and understanding the above description. The scope of the invention should, therefore, be determined with reference to the appended claims, along with the full scope of equivalents to which such claims are entitled.

What is claimed is:

1. A method for enhancing cell therapy of cardiac tissue, comprising:
   programming a pacing mode adapted to enhance the cell therapy and including a first type pacing therapy including specialized cell therapy pacing cycles and a second type pacing therapy;
   programming a duty cycle being a ratio of pacing of the first type pacing therapy to pacing of the second type pacing therapy; and
   applying electrical therapy using an implantable pulse generator to cardiac tissue administered with exogenous cell therapy comprising donor cells,
   wherein the electrical therapy includes the pacing mode and enhances one or more of engraftment, survival, proliferation, differentiation and function of the donor cells.

2. The method of claim 1, wherein the pacing therapy includes VDD pacing mode with an atrioventricular delay which is relatively short compared to an intrinsic atrioventricular interval.

3. The method of claim 2, wherein the atrioventricular delay is varied gradually over time.

4. The method of claim 1, wherein the electrical therapy is applied based on a level of activity.

5. The method of claim 1, wherein the electrical therapy is applied at predetermined times.

6. The method of claim 1, wherein the cardiac tissue is treated in vivo.

7. The method of claim 6, further comprising administering an agent that enhances exogenous cell engraftment, survival, proliferation, differentiation, or function.

8. The method of claim 6, further comprising administering an agent that enhances cardiac function.

9. The method of claim 6, further comprising administering an agent that enhances angiogenesis.

10. The method of claim 1, wherein the damaged cardiac tissue is human cardiac tissue.

11. The method of claim 1, wherein the donor cells include autologous cells.

12. The method of claim 1, wherein the donor cells include skeletal myoblasts.

13. The method of claim 1, wherein the donor cells are expanded in vitro prior to administration.

14. A system for electrical therapy of cardiac tissue of a heart, at least a portion of the cardiac tissue administered with exogenous cells in a cell therapy, comprising:
   one or more catheter leads with electrodes; and
   a pulse generator comprising an interface configured to connect to the one or more catheter leads, a controller programmable for a plurality of pulse delivery modes, and a sense amplifier for sensing electrical signals from the one or more catheter leads,
   the pulse generator programmed to include a selectable pacing mode adapted to enhance the cell therapy, the selectable pacing mode adapted to provide a first type pacing therapy and a second type pacing therapy delivered at a duty cycle being a ratio of pacing of the first type pacing therapy to pacing of the second type pacing therapy, the first type pacing therapy adapted to enhance the cell therapy and including the specialized cell therapy pacing cycles.

15. The system of claim 14, wherein the pulse generator includes a VDD pacing mode having an atrioventricular delay that is lengthened by the predetermined amount on the predetermined periodic basis over the predetermined time.

16. The system of claim 14, wherein the therapeutic electrical stimulation is provided at times between additional pacing and defibrillation therapies.

17. The system of claim 14, wherein the therapeutic electrical stimulation is programmable for certain times of day.

18. The system of claim 17, wherein the therapeutic electrical stimulation is programmable for sleep times.

19. The system of claim 14, wherein the therapeutic electrical stimulation is invoked by a programmer.

20. The system of claim 14, wherein accelerometer data is used to determine when to apply the therapeutic electrical stimulation.

21. The system of claim 14, wherein lead location is used to determine types of the therapeutic electrical stimulation.

22. The system of claim 14, wherein the first type pacing therapy is programmable for being invoked upon detection of a level of stress.

23. The system of claim 14, wherein the first type pacing therapy is programmable for being invoked upon detection of a level of activity.

* * * * *

UNITED STATES PATENT AND TRADEMARK OFFICE
CERTIFICATE OF CORRECTION

PATENT NO. : 7,627,373 B2  Page 1 of 1
APPLICATION NO. : 10/723258
DATED : December 1, 2009
INVENTOR(S) : Girouard et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 566 days.

Signed and Sealed this

Second Day of November, 2010

David J. Kappos
*Director of the United States Patent and Trademark Office*